US012459956B2

(12) United States Patent
deLong et al.

(10) Patent No.: US 12,459,956 B2
(45) Date of Patent: Nov. 4, 2025

(54) HETEROBICYCLIC CARBOXAMIDES AND USES THEREOF

(71) Applicant: ALCON INC., Fribourg (CH)

(72) Inventors: Mitchell A. deLong, Chapel Hill, NC (US); Jill M. Sturdivant, Chapel Hill, NC (US); Cynthia L. Lichorowic, Raleigh, NC (US); Heeren M. Gordhan, Durham, NC (US)

(73) Assignee: Alcon Inc., Fribourg (CH)

( * ) Notice: Subject to any disclaimer, the term of this patent is extended or adjusted under 35 U.S.C. 154(b) by 877 days.

(21) Appl. No.: 17/642,092

(22) PCT Filed: Sep. 11, 2020

(86) PCT No.: PCT/US2020/050554

§ 371 (c)(1),
(2) Date: Mar. 10, 2022

(87) PCT Pub. No.: WO2021/050994

PCT Pub. Date: Mar. 18, 2021

(65) Prior Publication Data

US 2023/0002404 A1 Jan. 5, 2023

Related U.S. Application Data

(60) Provisional application No. 62/900,263, filed on Sep. 13, 2019.

(51) Int. Cl.
*C07D 495/04* (2006.01)
*C07D 471/04* (2006.01)
*C07D 513/04* (2006.01)

(52) U.S. Cl.
CPC ......... *C07D 495/04* (2013.01); *C07D 471/04* (2013.01); *C07D 513/04* (2013.01)

(58) Field of Classification Search
CPC ... C07D 495/04; C07D 471/04; C07D 513/04
USPC .......................................................... 514/301
See application file for complete search history.

(56) References Cited

U.S. PATENT DOCUMENTS

| | | | | |
|---|---|---|---|---|
| 4,496,568 | A | 1/1985 | Maffrand et al. | |
| 4,839,365 | A * | 6/1989 | Hirai .................... | C07D 495/04 546/114 |
| 7,365,080 | B2 | 4/2008 | Gregor et al. | |
| 2018/0327381 | A1 | 11/2018 | deLong et al. | |

FOREIGN PATENT DOCUMENTS

| | | | |
|---|---|---|---|
| WO | 2021/050994 | A1 | 3/2021 |

OTHER PUBLICATIONS

International Search Report and Written Opinion, mailed on Feb. 1, 2021, for International Application Serial No. PCT/US2020/050554 filed on Sep. 11, 2020.
Pubchem. CID 49831050. Jan. 6, 2011, pp. 1.10. Retrieved from the Internet <URL: https://pubchem.ncbl.nlm.nlh.gov/compound/49831050>; p. 2, formula.
Pubchem. SID 194941076. Jul. 31, 2014, pp. 1-7. Retrieved from the Internet <URL: https://pubchem.ncbi.nlm.nlh.gov/substance/194941076/verslon/1 >; p. 2, formula.
Pubchem. SID 103627667. Dec. 22, 2010, pp. 1-7. Retrieved from the Internet <URL: https://pubchem .ncbl.nlm.nlh.gov/substance/103627667 /verslon/1 >; p. 2, formula.

* cited by examiner

*Primary Examiner* — Kristin A Vajda
(74) *Attorney, Agent, or Firm* — K&L Gates LLP; Louis C. Cullman; Benjamin D. Heuberger

(57) ABSTRACT

Provided herein are heterobicyclic cyclopropanecarboxamide and heterobicyclic carboxamide compounds. In particular, provided herein are compounds that affect the function of kinases in a cell, and that are useful as therapeutic agents or with therapeutic agents. The compounds provided herein are useful in the treatment of a variety of diseases and conditions including eye diseases such as glaucoma, cardiovascular diseases, inflammatory diseases, and diseases characterized by abnormal growth, such as cancers. Also provided herein are compositions comprising heterobicyclic cyclopropanecarboxamide or heterobicyclic carboxamide compounds.

45 Claims, No Drawings

Specification includes a Sequence Listing.

HETEROBICYCLIC CARBOXAMIDES AND USES THEREOF

RELATED APPLICATIONS

This application is a national stage entry under 35 USC § 371 of international application No. PCT/US2020/050554, filed Sep. 11, 2020, which claims priority of U.S. Provisional Patent Application No. 62/900,263, filed Sep. 13, 2019, the entire content of which is herein incorporated by reference.

SEQUENCE LISTING

This application contains a sequence listing having the filename 1959002-00266_ST25.txt, which is 655 bytes in size, and was created on Sep. 8, 2020. The entire content of this sequence listing is herein incorporated by reference.

FIELD OF THE INVENTION

The present disclosure relates to heterobicyclic cyclopropanecarboxamide compounds that affect the function of kinases and other proteins in a cell and that are useful as therapeutic agents or with therapeutic agents. In particular, these compounds are useful in the treatment of eye diseases such as glaucoma and retinal diseases, as anti-inflammatory agents, for the treatment of cardiovascular diseases, and for diseases characterized by abnormal growth, such as cancers.

BACKGROUND

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors. The biological effects of activating or inhibiting these receptors is not direct but is mediated by a host of intracellular proteins. The importance of these secondary proteins has been recognized and modulation of this class is now being investigated as intervention points in disease states. One of the most important classes of these downstream effectors is the "kinase" class.

The various kinases play important roles in the regulation of various physiological functions. For example, kinases have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis. The importance of p38 MAPK inhibitors in particular as new drugs for rheumatoid arthritis is reflected by the large number of compounds that has been developed over the last years (J. Westra and P. C. Limburg Mini-Reviews in Medicinal Chemistry Volume 6, Number 8, August 2006). Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (e.g., cardiac malformations), neurodegenerative diseases such as Parkinson's Disease and Alzheimer's Disease, multiple sclerosis, Epstein-Barr infection and cancer (*Nature Reviews Drug Discovery* 2002, 1: 493-502). In other disease states, the role of kinases is only now becoming clear. The retina is a complex tissue composed of multiple interconnected cell layers, highly specialized for transforming light and color into electrical signals that are perceived by the brain. Damage or death of the primary light-sensing cells, the photoreceptors, results in devastating effects on vision. Despite the identification of numerous mutations that cause inherited retinal degenerations, the cellular and molecular mechanisms leading from the primary mutations to photoreceptor apoptosis are not well understood but may involve the wnt pathway (A S Hackam "The Wnt Signaling Pathway in Retinal Degeneration" *IUBMB Life* Volume 57, Number 6/June 2005).

The success of the tyrosine-kinase inhibitor ST1571 (Gleevec) in the treatment of chronic myelogenous leukemia (*Nature Reviews Drug Discovery* 2003, 2: 296-313) has spurred considerable efforts to develop other kinase inhibitors for the treatment of a wide range of other cancers (*Nature Reviews Cancer* 2003, 3: 650-665). The balance between the initiation and the inactivation of intracellular signals determines the intensity and duration of the response of the receptors to stimuli such as agonists. When desensitization occurs, the mediation or regulation of the physiological function mediated or regulated by the G proteins to which the receptors are coupled is reduced or prevented. For example, when agonists are administered to treat a disease or condition by activation of certain receptors, the receptors relatively quickly become desensitized from the action of the GRKs such that agonist administration may no longer result in therapeutic activation of the appropriate receptors. At that point, administration of the agonist no longer enables sufficient or effective control of or influence on the disease or condition intended to be treated.

Janus Kinases (or JAK) are a family of cytoplasmic protein tyrosine kinases. The JAK family plays a role in the cytokine-dependent regulation of proliferation and function of cells involved in immune response. Currently, there are four JAK family members are known JAK1, JAK2, JAK3, and TYK2. The JAKs usually associate with cytokine receptors in pairs as homodimers or heterodimers. Specific cytokines are associated with specific JAK pairings. Each of the four members of the JAK family is implicated in the signaling of at least one of the cytokines associated with inflammation. Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. There is recent evidence that the kinases ROCK1 and ROCK2 may also participate in similar interactions with the STAT enzymes. Inhibition of ROCK kinases has been noted to have an anti-inflammatory effect as well.

In view of the role that kinases play in many disease states, there is an urgent and continuing need for small molecule ligands which inhibit or modulate the activity of kinases. Without wishing to be bound by theory, it is thought that modulation of the activity of kinases, in particular ROCK and JAK kinases, by the compounds of the present disclosure is, at least in part, responsible for their beneficial effects.

SUMMARY

In one aspect, provided herein are compounds of the formula:

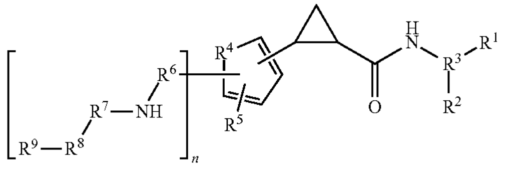

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

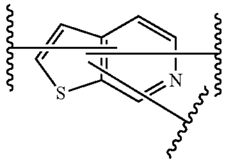,
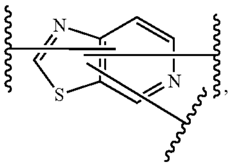, or
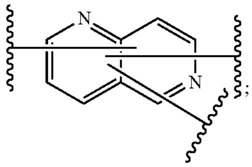;

$R^4$ is S, —C(H)═C(H)—, or —C(H)═N—;

$R^5$ is H or halogen;

$R^6$ is CO or $SO_2$;

$R^7$ is a bond or $CH_2$;

$R^8$ is $CH_2$, phenyl, or a monocyclic $C_{3-5}$ heteroaryl having 1-3 heteroatoms, wherein each heteroatom is, independently, N, O, or S;

$R^9$ is H, halogen, CN, $NH_2$, OH, $C_{1-6}$ alkyl, $C_{1-6}$ alkyl-CN, $C_{1-6}$ haloalkyl, O—($C_{1-6}$ alkyl), O—($C_{1-6}$ haloalkyl), or $C_{3-6}$ cycloalkyl; and n is 0 or 1; or

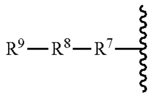

is H, and $R^{1-6}$ and n are as defined above.

In another aspect, provided herein are compounds of the formula:

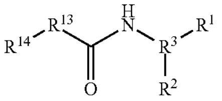

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

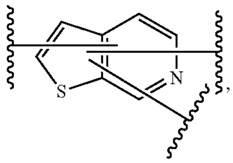,
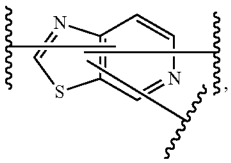, or
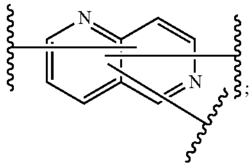;

$R^{13}$ is $CH_2$, $CH_2NH$,

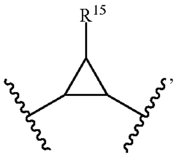,
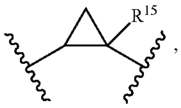,
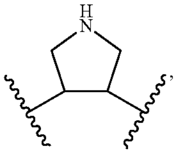,
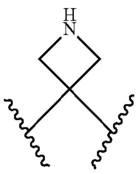,
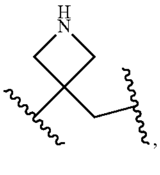,
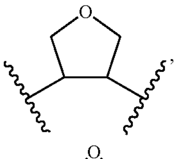,
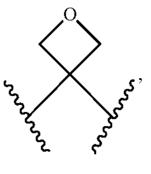,
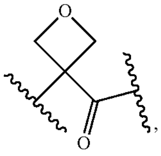,
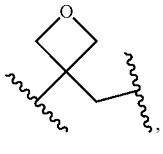, or
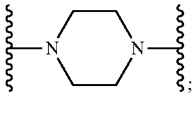;

$R^{14}$ is H, OH, $NH_2$, CN, $C_{1-3}$ alkyl, phenyl, phenyl-$CH_3$, $CH_2$-phenyl, phenyl-(O—$C_{1-6}$ alkyl), $SO_2$—($C_{1-6}$ alkyl), $CHCH_2$, $C_{1-3}$ alkylene-CN, $C_{1-6}$ alkyl-OH, $C_{1-6}$ alkyl-$NH_2$, a monocyclic $C_{3-5}$ heterocycloalkyl having 1-3 (e.g., 1 or 2, e.g., 1) heteroatoms, or a monocyclic $C_{3-5}$ heteroaryl having 1-3 heteroatoms, wherein each heteroatom is, independently, N, O, or S (e.g., N or O, e.g., N, e.g., O), and wherein each heteroaryl may be substituted with one or two halogen substituents; and $R^{15}$ is H, CN, OH, or $NH_2$.

In another aspect, provided herein are compounds of the formula:

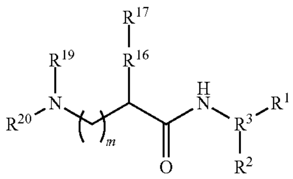

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

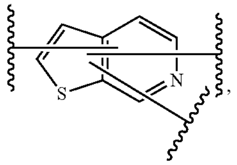,
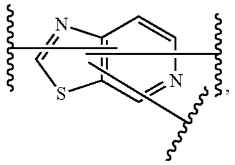, or

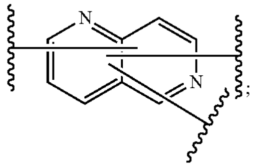;

$R^{16}$ is phenyl, $CH_2$-phenyl, a $CH_2$-monocyclic $C_{3-5}$ heteroaryl having 1-3 heteroatoms, or a monocyclic $C_{3-5}$ heteroaryl having 1-3 heteroatoms, wherein each heteroatom is, independently, N, O, or S, and wherein each heteroaryl may be substituted with one or two halogen substituents;

$R^{17}$ is H, OH, halogen, $C_{1-6}$ alkyl-OH, $C_{1-6}$ alkyl-O—C(O)-phenyl-$(R^{18})_z$;

$R^{18}$ is H, OH, halogen, or $C_{1-6}$ alkyl;

$R^{19}$ is H or $C_{1-6}$ alkyl;

$R^{20}$ is H or $C_{1-6}$ alkyl;

z is 0, 1, 2, 3, 4, or 5; and m is 0, 1, or 2.

In another aspect, the present disclosure provides a pharmaceutical composition comprising a compound according to the present disclosure and a pharmaceutically acceptable excipient.

In another aspect, the present disclosure provides a method of treating an ocular disorder in a subject in need of treatment, comprising administering to the subject a compound or composition according to the present disclosure.

In another aspect, the present disclosure provides a method of reducing intraocular pressure in a subject in need thereof, comprising administering to an eye of the subject a compound or composition according to the present disclosure.

In another aspect, the present disclosure provides a kit comprising a compound or composition according to the present disclosure and instructions for use.

DETAILED DESCRIPTION

Publications and patents are referred to throughout this disclosure. All U.S. Patents cited herein are hereby incorporated by reference. All percentages, ratios, and proportions used herein are percent by weight unless otherwise specified.

Heterobicyclic cyclopropanecarboxamides are provided herein.

As used herein, the term "alkyl" refers to a saturated aliphatic hydrocarbon including straight chain and branched chain groups. "Alkyl" may be exemplified by groups such as methyl, ethyl, n-propyl, isopropyl, n-butyl and the like. "$C_{1-6}$ alkyl" refers to alkyl groups containing one to six carbon atoms.

As used herein, the term "contacting a cell" is used to mean contacting a cell in vitro or in vivo i.e. in a subject, such as a mammal, including humans, rabbits, cats and dogs.

As used herein, the term "controlling the disease or condition" is used to mean changing the activity of one or more kinases to affect the disease or condition.

As used herein, the term "disease or condition associated with kinase activity" is used to mean a disease or condition treatable, in whole or in part, by inhibition of one or more kinases.

As used herein, the term "excipient" includes physiologically compatible additives useful in preparation of a pharmaceutical composition. Examples of pharmaceutically acceptable carriers and excipients can for example be found in Remington Pharmaceutical Science, 16$^{th}$ Ed.

As used herein, the term "eye disease" includes, but is not limited to, glaucoma, allergy, cancers of the eye, neurodegenerative diseases of the eye, such as diabetic eye disease, macular degeneration (AMD), inflammation, and dry eye.

As used herein, the term "halogen" refers to fluoro, chloro, bromo or iodo moieties. In some embodiments, the halogen is fluoro, chloro, or bromo. In some embodiments, the halogen is fluoro.

As used herein, the term "haloalkyl" refers to an alkyl group substituted with one or more (e.g., 1, 2, 3, 4, 5, 6, 7, 8, 9, 10 or more) halogens, each independently selected from fluoro, chloro, bromo or iodo.

As used herein, the term "heteroaryl" refers to an aromatic carbocyclic radical having one or more heteroatoms in the carbocyclic ring.

As used herein, the term "pharmaceutically acceptable carrier" means a carrier that is useful for the preparation of a pharmaceutical composition that is: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

As used herein, "pharmaceutically acceptable salts" refers to an ionizable therapeutic agent that has been combined with a counter-ion to form a neutral complex. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

"Treatment" of an individual or a cell is any type of intervention provided as a means to alter the natural course of a disease or pathology in the individual or cell. Treatment includes, but is not limited to, administration of, e.g., a pharmaceutical composition, and may be performed either prophylactically, or subsequent to the initiation of a pathologic event or contact with an etiologic agent. Treatment includes any desirable effect on the symptoms or pathology of a disease or condition associated with inflammation, among others described herein.

Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

As used herein, the term "therapeutically effective amount" as used herein refers to a dosage of the compounds or compositions effective for influencing, reducing or inhibiting the activity of or preventing activation of a kinase. This term as used herein may also refer to an amount effective at bringing about a desired in vivo effect in an animal, preferably, a human, such as reduction in intraocular pressure.

Compounds

In one aspect, provided herein are compounds of the formula:

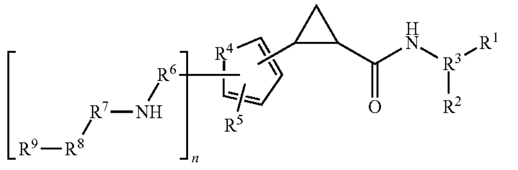

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

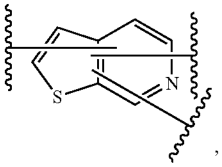
,
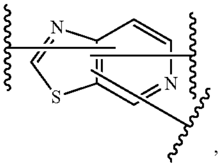
, or
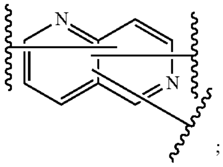
;

$R^4$ is S, —C(H)═C(H)—, or —C(H)═N—;

$R^5$ is H or halogen;

$R^6$ is CO or $SO_2$;

$R^7$ is a bond or $CH_2$;

$R^8$ is $CH_2$, phenyl, or a monocyclic $C_{3-5}$ heteroaryl having 1-3 heteroatoms, wherein each heteroatom is, independently, N, O, or S;

$R^9$ is H, halogen, CN, $NH_2$, OH, $C_{1-6}$ alkyl, $C_{1-6}$ alkyl-CN, $C_{1-6}$ haloalkyl, O—($C_{1-6}$ alkyl), O—($C_{1-6}$ haloalkyl), or $C_{3-6}$ cycloalkyl; and n is 0 or 1; or

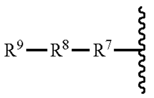

is H, and $R^{1-6}$ and n are as defined above.

In one aspect, provided herein are compounds of the formula:

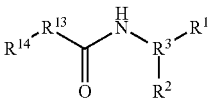

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

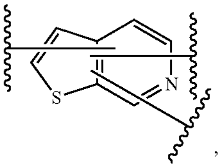
,
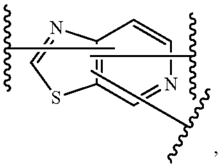
, or
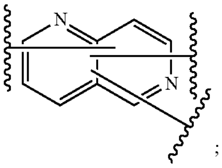
;

$R^{13}$ is $CH_2$, $CH_2NH$,

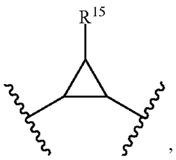
,
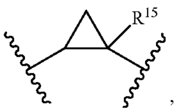
,
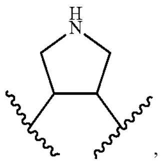
,
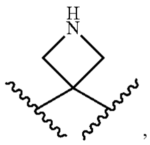
,
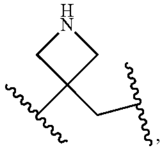
,
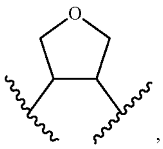
,

-continued

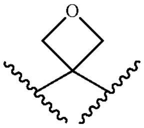, 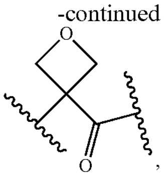, 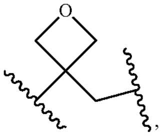, or

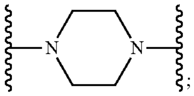;

$R^{14}$ is H, OH, $NH_2$, CN, $C_{1-3}$ alkyl, phenyl, phenyl-$CH_3$, $CH_2$-phenyl, phenyl-(O—$C_{1-6}$ alkyl), $SO_2$—($C_{1-6}$ alkyl), $CHCH_2$, $C_{1-3}$ alkylene-CN, $C_{1-6}$ alkyl-OH, $C_{1-6}$ alkyl-$NH_2$, a monocyclic $C_{3-5}$ heterocycloalkyl having 1-3 (e.g., 1 or 2, e.g., 1) heteroatoms, or a monocyclic $C_{3-5}$ heteroaryl having 1-3 heteroatoms, wherein each heteroatom is, independently, N, O, or S (e.g., N or O, e.g., N, e.g., O), and wherein each heteroaryl may be substituted with one or two halogen substituents; and $R^{15}$ is H, CN, OH, or $NH_2$.

In some embodiments,

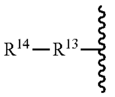

comprises 1 chemical ring. In some embodiments,

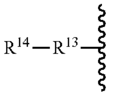

comprises 2 chemical rings.

In another aspect, provided herein are compounds of the formula:

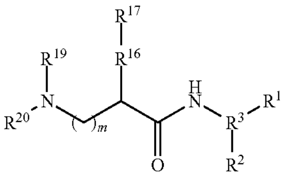

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

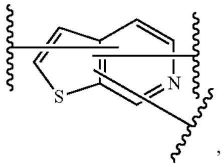, 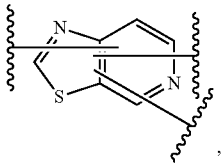, or

-continued

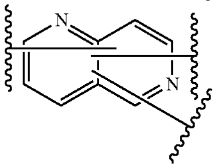;

$R^{16}$ is phenyl, $CH_2$-phenyl, a $CH_2$-monocyclic $C_{3-5}$ heteroaryl having 1-3 heteroatoms, or a monocyclic $C_{3-5}$ heteroaryl having 1-3 heteroatoms, wherein each heteroatom is, independently, N, O, or S, and wherein each heteroaryl may be substituted with one or two halogen substituents;

$R^{17}$ is H, OH, halogen, $C_{1-6}$ alkyl-OH, $C_{1-6}$ alkyl-O—C(O)-phenyl-$(R^{18})_z$;

$R^{18}$ is H, OH, halogen, or $C_{1-6}$ alkyl;

$R^{19}$ is H or $C_{1-6}$ alkyl;

$R^{20}$ is H or $C_{1-6}$ alkyl;

z is 0, 1, 2, 3, 4, or 5; and m is 0, 1, or 2.

In some embodiments of the formulae provided herein, the compounds are of the formula:

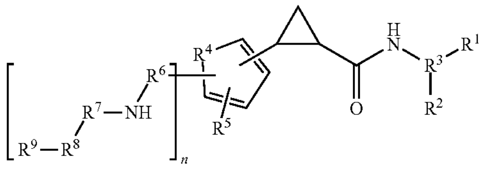

or a pharmaceutically acceptable salt thereof, wherein $R^1$ is H, F, Cl, Br, I, CN, $NH_2$, OH, $OCF_3$, $OCH_2CF_3$, $C_{1-6}$ alkyl, $C_{3-6}$ cycloalkyl, or $C_{1-6}$ haloalkyl;

$R^2$ is H, F, Cl, Br, I, $C_{1-6}$ alkyl, or $C_{1-6}$ haloalkyl;

$R^3$ is

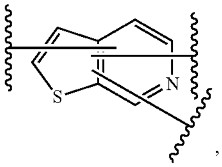, 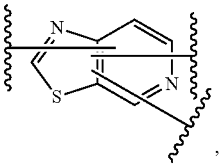, or

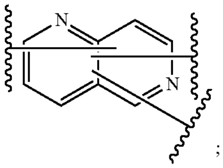;

$R^4$ is S, —C(H)═C(H)—, or —C(H)═N—;

$R^5$ is H, F, Cl, Br, or I;

$R^6$ is CO or $SO_2$;

$R^7$ is a bond or $CH_2$;

$R^8$ is phenyl, or a monocyclic $C_{3-5}$ heteroaryl having 1-3 heteroatoms, wherein each heteroatom is, independently, N, O, or S; when $R^7$ is not H $R^9$ is H, F, Cl, Br, I, $C_{1-6}$ alkyl, or $C_{1-6}$ haloalkyl when $R^7$ is not H; and n is 0 or 1; or

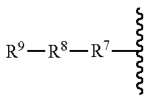

is H, and $R^{1-6}$ and n are as defined above.

In some embodiments of the formulae provided herein, the compounds are of the formula:

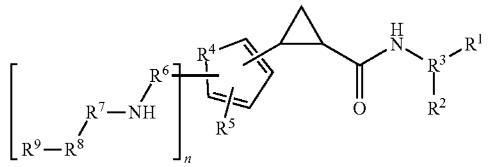

or a pharmaceutically acceptable salt thereof, wherein $R^1$ is H, F, Cl, Br, I, CN, $NH_2$, OH, $OCF_3$, $OCH_2CF_3$, $C_{1-6}$ alkyl, $C_{3-6}$ cycloalkyl, or $C_{1-6}$ haloalkyl;

$R^2$ is H, F, Cl, Br, I, $C_{1-6}$ alkyl, or $C_{1-6}$ haloalkyl;

$R^3$ is

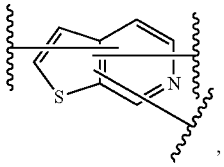

,

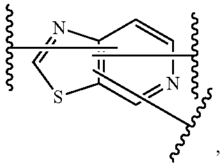

, or

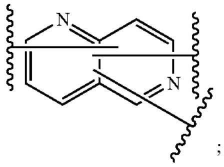

;

$R^4$ is S, —C(H)═C(H)—, or —C(H)═N—;

$R^5$ is H, F, Cl, Br, or I;

$R^6$ is CO or $SO_2$;

$R^7$ is a bond or $CH_2$;

$R^8$ is phenyl, or a monocyclic $C_{3-5}$ heteroaryl having 1-3 heteroatoms, wherein each heteroatom is, independently, N, O, or S;

$R^9$ is H, F, Cl, Br, I, $C_{1-6}$ alkyl, or $C_{1-6}$ haloalkyl; and n is 0 or 1.

In some embodiments, provided herein are compounds of the formula:

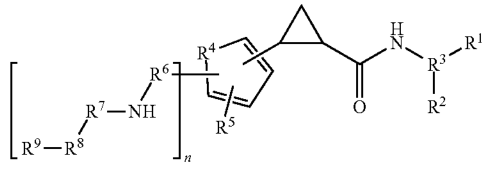

or a pharmaceutically acceptable salt thereof, wherein $R^1$ is H, F, Cl, Br, I, $C_{1-6}$ alkyl, or $C_{1-6}$ haloalkyl;

$R^2$ is H, F, Cl, Br, I, $C_{1-6}$ alkyl, or $C_{1-6}$ haloalkyl;

$R^3$ is

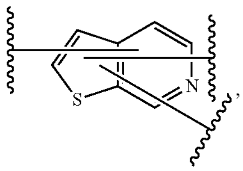

,

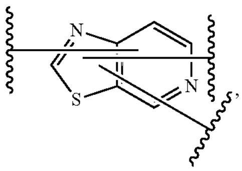

, or

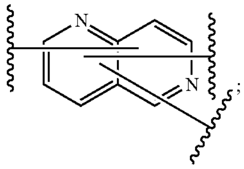

;

$R^4$ is S, —C(H)═C(H)—, or —C(H)═N—;

$R^5$ is H, F, Cl, Br, or I;

$R^6$ is CO or $SO_2$;

$R^7$ is a bond or $CH_2$;

$R^8$ is phenyl, or a monocyclic $C_{3-5}$ heteroaryl having 1-3 heteroatoms, wherein each heteroatom is, independently, N, O, or S;

$R^9$ is H, F, Cl, Br, I, $C_{1-6}$ alkyl, or $C_{1-6}$ haloalkyl; and n is 0 or 1; or

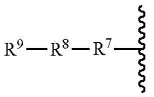

is H, and $R^{1-6}$ and n are as defined above.

In some embodiments of the formulae provided herein, the compound is of the formula:

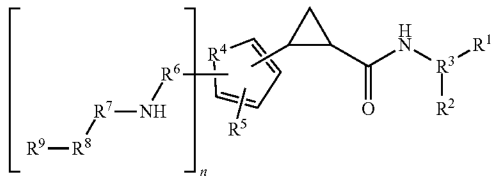

or a pharmaceutically acceptable salt thereof, wherein $R^1$ is H, F, Cl, Br, I, $C_{1-6}$ alkyl, or $C_{1-6}$ haloalkyl;

$R^2$ is H, F, Cl, Br, I, $C_{1-6}$ alkyl, or $C_{1-6}$ haloalkyl;

$R^3$ is

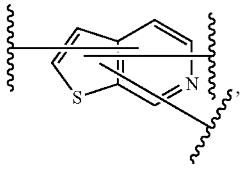

,

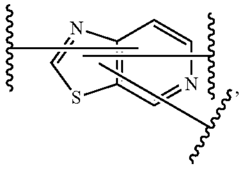

, or

-continued

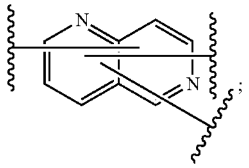

$R^4$ is S, —C(H)=C(H)—, or —C(H)=N—;

$R^5$ is H, F, Cl, Br, or I;

$R^6$ is CO or $SO_2$;

$R^7$ is a bond or $CH_2$;

$R^8$ is phenyl, or a monocyclic $C_{3-5}$ heteroaryl having 1-3 heteroatoms, wherein each heteroatom is, independently, N, O, or S;

$R^9$ is H, F, Cl, Br, I, $C_{1-6}$ alkyl, or $C_{1-6}$ haloalkyl; and n is 0 or 1.

In some embodiments of the formulae provided herein, the compound is a compound of the formula selected from:

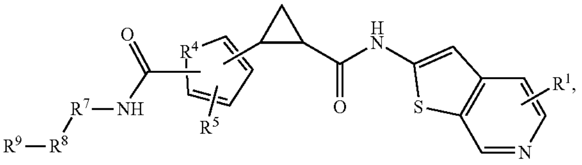

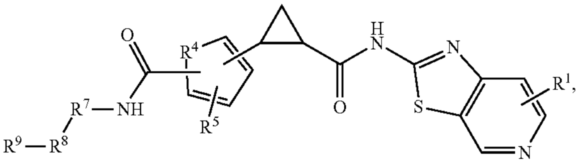

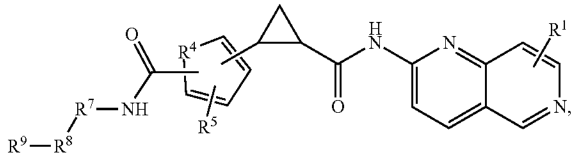

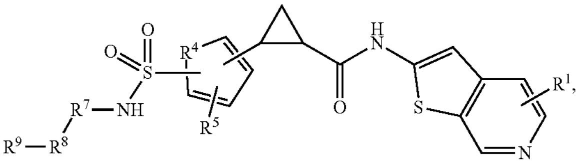

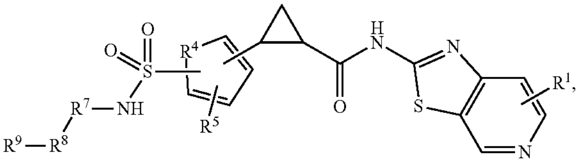

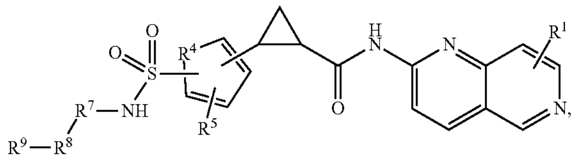

or a pharmaceutically acceptable salt thereof.

In some embodiments, the compound is of the formula:

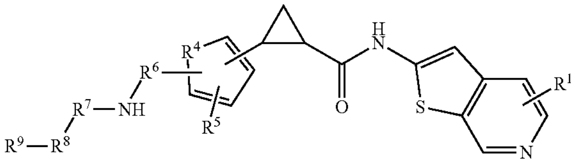

or a pharmaceutically acceptable salt thereof.

In some embodiments, the compound is of the formula:

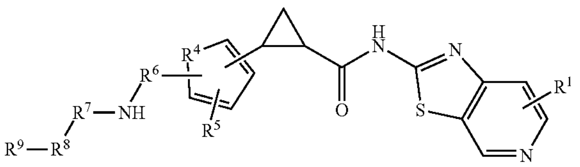

or a pharmaceutically acceptable salt thereof.

In some embodiments, the compound is of the formula:

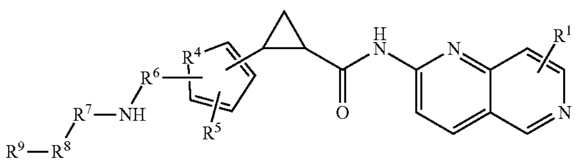

or a pharmaceutically acceptable salt thereof.

In some embodiments, the compound is of the formula:

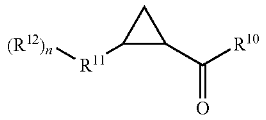

or a pharmaceutically acceptable salt thereof, wherein n is 1;

$R^{10}$ is

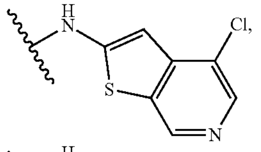

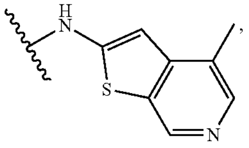

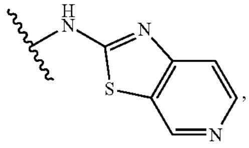

, or

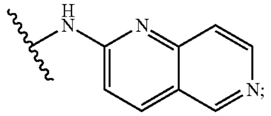

$R^{11}$ and $R^{12}$ are connected by an amide or sulfonamide linkage;

$R^{12}$ is

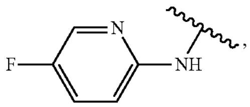,
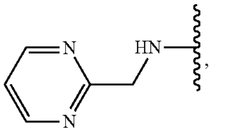,
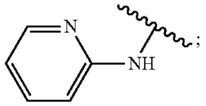;

and $R^{11}$ is

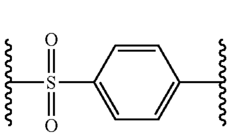
or
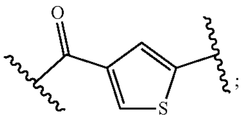;

or n is 0, $R^{10}$ and $R^{12}$ are as defined above, and $R^{11}$ is

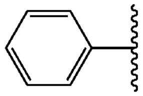
or
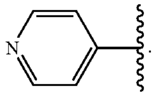.

In some embodiments, the compound is a compound of the formula:

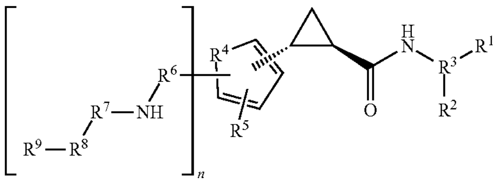

or a pharmaceutically acceptable salt thereof,

In some embodiments, the compound is a compound of the formula selected from:

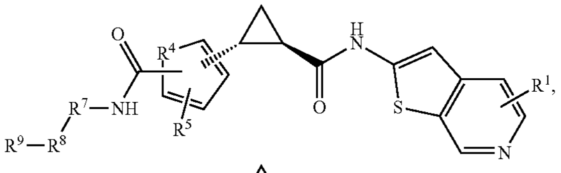,

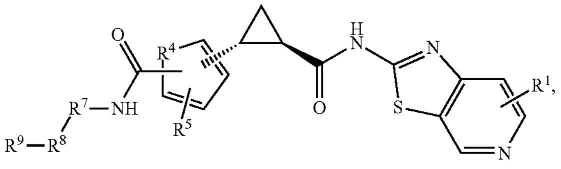,

-continued

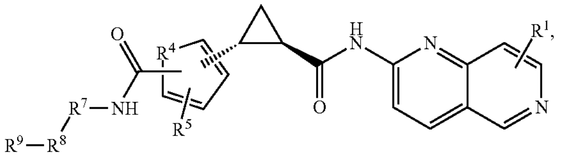,

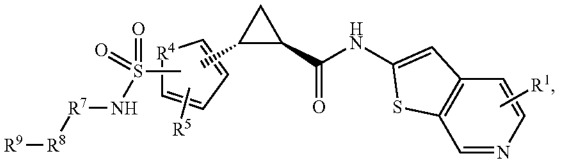,

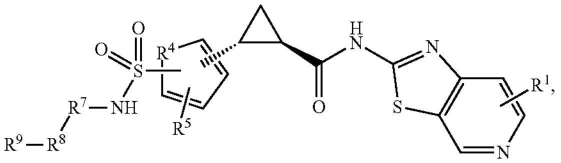,

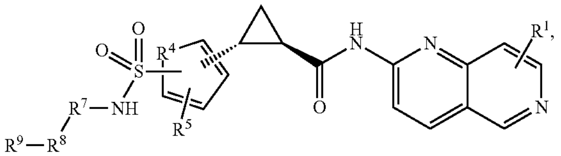, or a pharmaceutically acceptable salt thereof.

In some embodiments, the compound is of the formula:

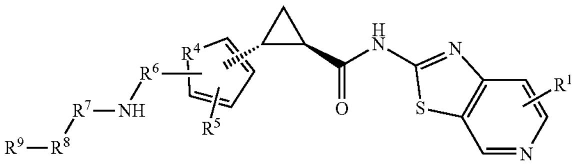

or a pharmaceutically acceptable salt thereof.

In some embodiments, the compound is of the formula:

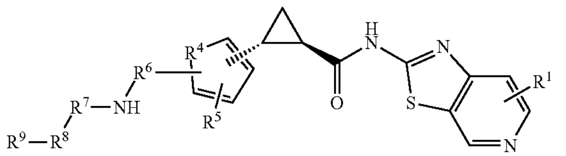

or a pharmaceutically acceptable salt thereof.

In some embodiments, the compound is of the formula:

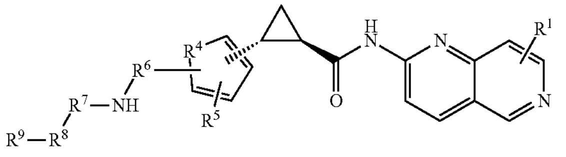

or a pharmaceutically acceptable salt thereof.

In some embodiments, the compound is of the formula:

(I-11)

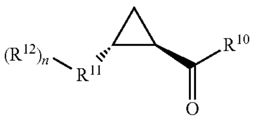

or a pharmaceutically acceptable salt thereof.

In some embodiments of the formulae provided herein:

$R^1$ is H, F, Cl. Me, CN, or $C_{1-3}$ alkyl;

$R^2$ is H, F, or $C_{1-3}$ alkyl; or $R^9$ is H, F, or $C_{1-3}$ alkyl.

In some embodiments

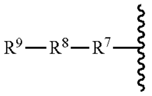

is H. In some embodiments

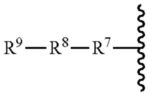

is H, and n is 1.

In some embodiments $R^1$ is H, Br, Cl, F, Me, Et, iPr, Pr, nBu, iBu, sBu, cyclopropyl, cyclobutyl, cyclopentyl, cyclohexyl, —$CHF_2$, —$CF_3$, —$OCF_3$, —$CH_2CF_3$, —CN, —$CH_2CN$, —$NH_2$, —OH, —$CH_2OH$, or —$CH_2NH_2$.

In some embodiments $R^4$ is S.

In some embodiments $R^4$ is —C(H)=C(H)—.

In some embodiments $R^4$ is —C(H)=N—.

In some embodiments $R^6$ is CO.

In some embodiments $R^6$ is $SO_2$.

In some embodiments $R^7$ is a bond.

In some embodiments $R^7$ is a $CH_2$.

In some embodiments $R^1$ is H, $R^5$ is H, or $R^9$ is H.

In some embodiments $R^8$ is phenyl.

In some embodiments $R^8$ is a monocyclic $C_{3-5}$ heteroaryl having 1-3 heteroatoms, wherein each heteroatom is, independently, N, O, or S.

In some embodiments $R^8$ is a monocyclic $C_{3-5}$ heteroaryl having 1-3 nitrogen atoms.

In some embodiments $R^8$ is a pyridyl, pyrrolyl, furanyl, thiophenyl, pyrazolyl, imidazolyl, pyrimidinyl, triazinyl, thiazolyl, pyrazinyl, pyridazinyl, or oxazolyl.

In some embodiments $R^{14}$ is a pyridyl, pyrrolyl, furanyl, thiophenyl, pyrazolyl, imidazolyl, pyrimidinyl, triazinyl, thiazolyl, pyrazinyl, pyridazinyl, or oxazolyl.

In some embodiments $R^{16}$ is a pyridyl, pyrrolyl, furanyl, thiophenyl, pyrazolyl, imidazolyl, pyrimidinyl, triazinyl, thiazolyl, pyrazinyl, pyridazinyl, or oxazolyl.

In some embodiments the heteroaryl is a pyridyl, pyrrolyl, furanyl, thiophenyl, pyrazolyl, imidazolyl, pyrimidinyl, triazinyl, thiazolyl, pyrazinyl, pyridazinyl, or oxazolyl.

In some embodiments:

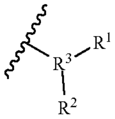 is

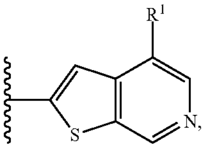 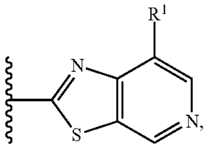 or

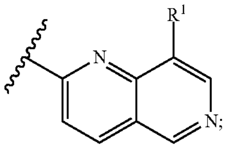

$R^1$ is H, Cl, or $CH_3$;

$R^4$ is S, —C(H)=C(H)—, or —C(H)=N—;

$R^5$ is H;

$R^6$ is CO or $SO_2$;

$R^7$ is a bond or $CH_2$;

$R^8$ is phenyl, or a monocyclic $C_{4-5}$ heteroaryl having 1 or 2 nitrogen atoms;

$R^9$ is H or F; and n is 1.

In some embodiments:

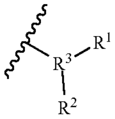 is

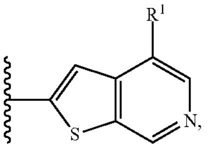 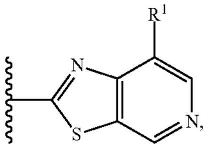 or

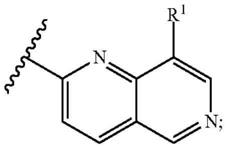

$R^1$ is H, Br, Cl, F, Me, Et, iPr, Pr, nBu, iBu, sBu, cyclopropyl, cyclobutyl, cyclopentyl, cyclohexyl, —$CHF_2$, —$CF_3$, —$OCF_3$, —$CH_2CF_3$, —CN, —$CH_2CN$, —$NH_2$, —OH, —$CH_2OH$, or —$CH_2NH_2$;

$R^4$ is S, —C(H)=C(H)—, or —C(H)=N—;

$R^5$ is H;

$R^6$ is CO or $SO_2$;

$R^7$ is a bond or $CH_2$;

$R^8$ is phenyl, or a monocyclic $C_{4-5}$ heteroaryl having 1 or 2 nitrogen atoms;

$R^9$ is H or F; and n is 1.

In some embodiments:

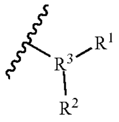

is

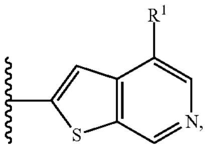

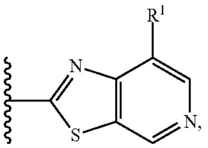

or

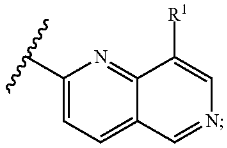

$R^1$ is H, Br, Cl, F, Me, Et, iPr, Pr, nBu, iBu, sBu, cyclopropyl, cyclobutyl, cyclopentyl, cyclohexyl, —$CHF_2$, —$CF_3$, —$OCF_3$, —$CH_2CF_3$, —CN, —$CH_2CN$, —$NH_2$, —OH, —$CH_2OH$, or —$CH_2NH_2$;

$R^4$ is S, —C(H)═C(H)—, or —C(H)═N—;

$R^5$ is H;

$R^6$ is CO or $SO_2$;

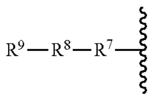

is H; and n is 1.

In some embodiments:

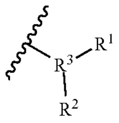

is

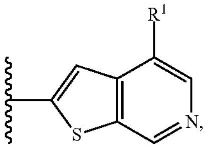

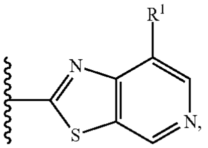

or

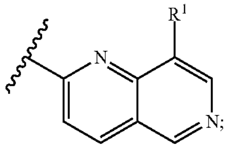

$R^1$ is H, Cl, or $CH_3$;

$R^4$ is —C(H)═C(H)— or —C(H)═N—;

$R^5$ is H; and n is 0.

In some embodiments:

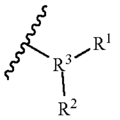

is

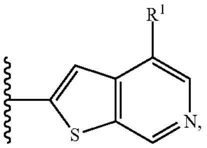

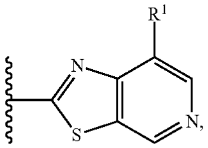

or

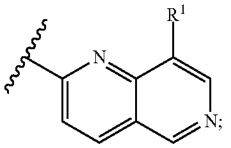

$R^1$ is H, Br, Cl, F, Me, Et, iPr, Pr, nBu, iBu, sBu, cyclopropyl, cyclobutyl, cyclopentyl, cyclohexyl, —$CHF_2$, —$CF_3$, —$OCF_3$, —$CH_2CF_3$, —CN, —$CH_2CN$, —$NH_2$, —OH, —$CH_2OH$, or —$CH_2NH_2$;

$R^4$ is —C(H)═C(H)— or —C(H)═N—;

$R^5$ is H; and n is 0.

In some embodiments $R^{13}$ is $CH_2$ or $CH_2NH$.

In some embodiments, $R^{13}$ is

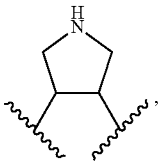,
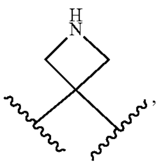,
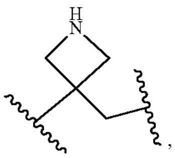,
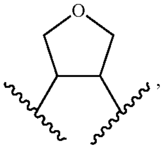,
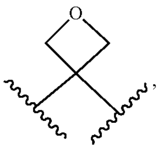,
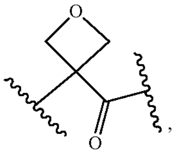,
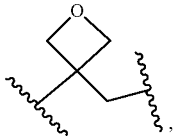, or
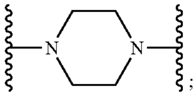;

In some embodiments, $R^{13}$ is

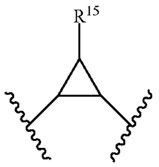

or

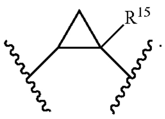.

In some embodiments $R^{14}$ is H, OH, $NH_2$, CN, $C_{1-3}$ alkyl, $SO_2$—($C_{1-6}$ alkyl), $CHCH_2$, $C_{1-3}$ alkylene-CN, $C_{1-6}$ alkyl-OH, or $C_{1-6}$ alkyl-$NH_2$.

In some embodiments $R^{14}$ is OH, $NH_2$, CN, $C_{1-3}$ alkyl, phenyl, phenyl-$CH_3$, $CH_2$-phenyl, phenyl-(O—$C_{1-6}$ alkyl), $SO_2$—($C_{1-6}$ alkyl), $CHCH_2$, $C_{1-3}$ alkylene-CN, $C_{1-6}$ alkyl-OH, $C_{1-6}$ alkyl-$NH_2$, a monocyclic $C_{3-5}$ heterocycloalkyl having 1-3 (e.g., 1 or 2, e.g., 1) heteroatoms, or a monocyclic $C_{3-5}$ heteroaryl having 1-3 heteroatoms, wherein each heteroatom is, independently, N, O, or S (e.g., N or O, e.g., N, e.g., O), and wherein each heteroaryl may be substituted with one or two halogen substituents.

In some embodiments $R^{14}$ is phenyl, phenyl-$CH_3$, $CH_2$-phenyl, phenyl-(O—$C_{1-6}$ alkyl), a monocyclic $C_{3-5}$ heterocycloalkyl having 1-3 (e.g., 1 or 2, e.g., 1) heteroatoms, or a monocyclic $C_{3-5}$ heteroaryl having 1-3 heteroatoms, wherein each heteroatom is, independently, N, O, or S (e.g., N or O, e.g., N, e.g., O), and wherein each heteroaryl may be substituted with one or two halogen substituents.

In some embodiments $R^{15}$ is CN, OH, or $NH_2$. In some embodiments $R^{15}$ is H.

In some embodiments $R^{16}$ is phenyl, or $CH_2$-phenyl.

In some embodiments $R^{16}$ is a $CH_2$-monocyclic $C_{3-5}$ heteroaryl having 1-3 heteroatoms, or a monocyclic $C_{3-5}$ heteroaryl having 1-3 heteroatoms, wherein each heteroatom is, independently, N, O, or S, and wherein each heteroaryl may be substituted with one or two halogen substituents.

In some embodiments $R^{17}$ is H, OH, halogen, or $C_{1-6}$ alkyl-OH.

In some embodiments $R^{17}$ is $C_{1-6}$ alkyl-OH or $C_{1-6}$ alkyl-O—C(O)-phenyl-$(R^{18})_z$.

In some embodiments $R^{17}$ is $C_{1-6}$ alkyl-O—C(O)-phenyl-$(R^{18})_z$.

In some embodiments z is 1 or 2. In some embodiments, z is 0.

In some embodiments m is 1 or 2. In some embodiments m is 0

In some embodiments the compound is a compound provided in a Table herein, or a pharmaceutically acceptable salt thereof.

In some embodiments the compound is:

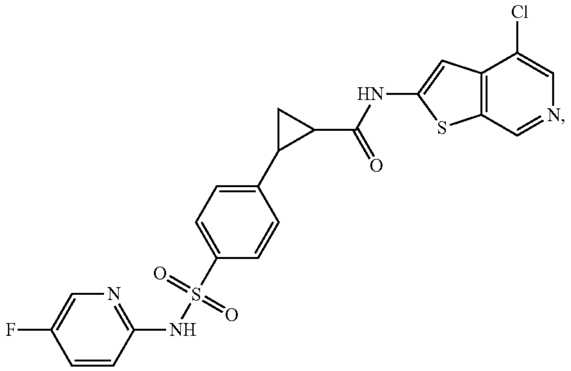

,

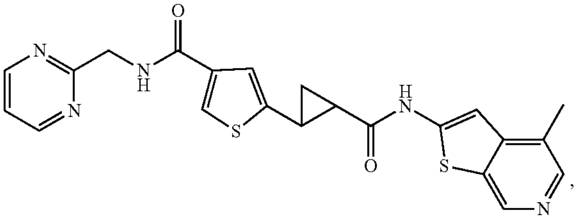

,

-continued

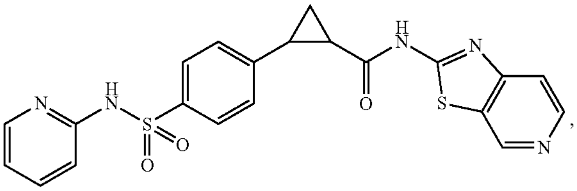

,

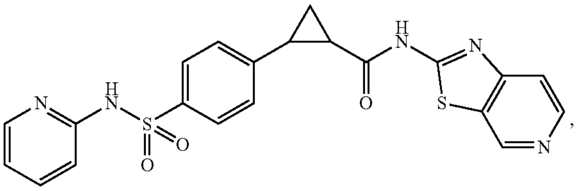

,

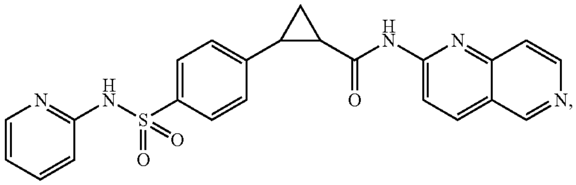

,

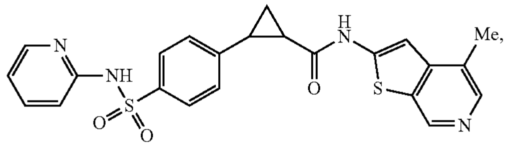

,

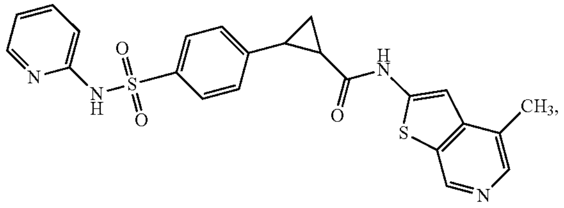

,

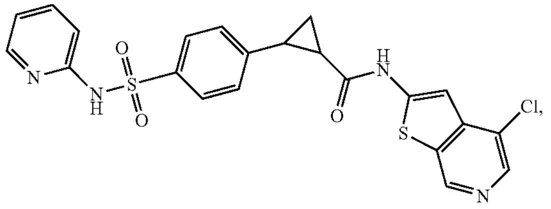

,

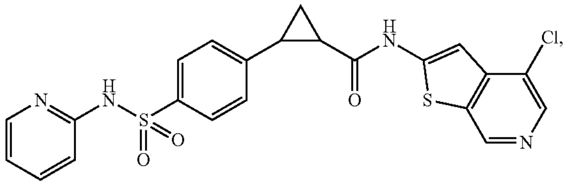

,

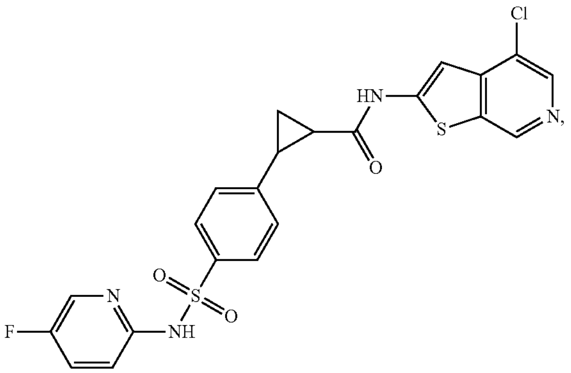

,

-continued
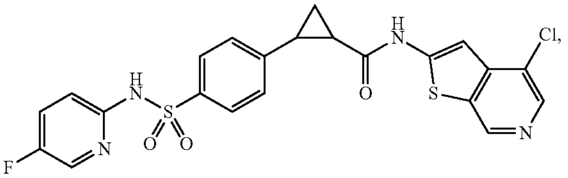
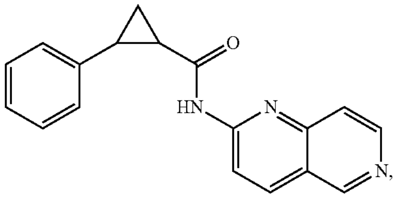
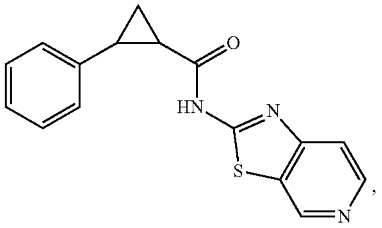
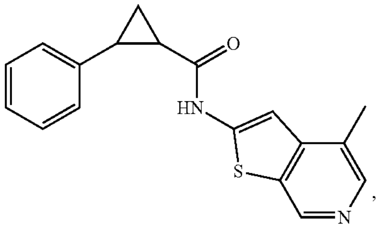
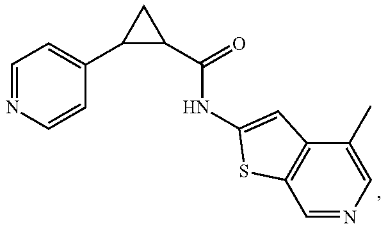
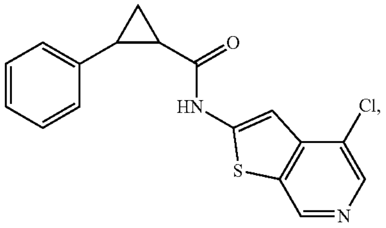
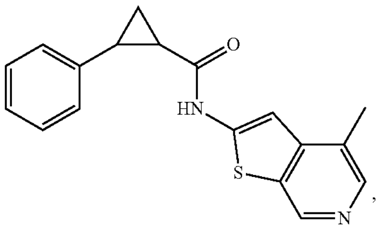
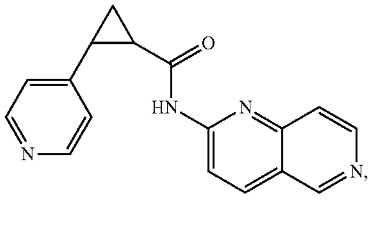
-continued
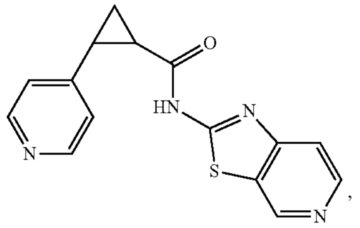
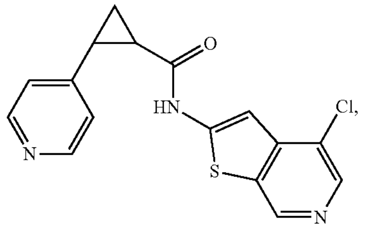
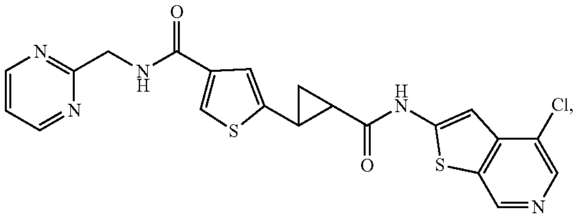
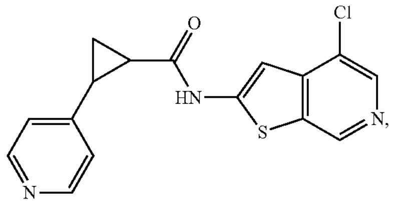
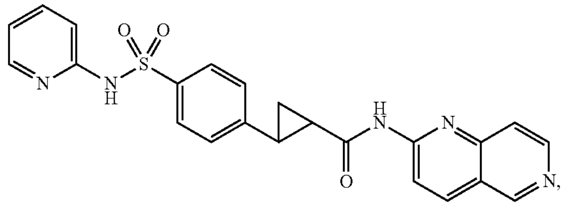
or a pharmaceutically acceptable salt thereof.
In some embodiments of the formulae provided herein, the formula is trans racemic or trans-R,R with respect to the cyclopropane stereocenters.
General Scheme for the Coupling of 1,6-Naphthyridin-2-Amine to Carboxylic Acid:
Scheme 1
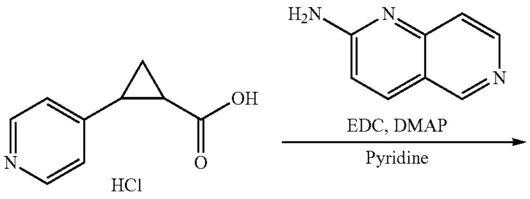
S1-1

-continued

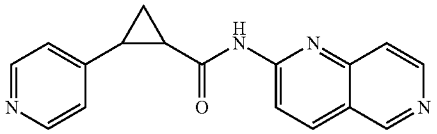

S1-2
53%

N-(1,6-naphthyridin-2-yl)-2-(pyridine-4-yl)cyclopropane-1-carboxamide (S1-2). To 2-(pyridine-4-yl)cyclopropane-1-carboxylic acid S1-1 (1.0 eq) was charged 1,6 naphthyridin-2-amine (1.0 eq), EDC (1.6 eq), HOBt (1.6 eq), DMAP (0.2 eq), and pyridine (1.0 mL). Stirred at 70 deg Celsius overnight. Poured into saturated aqueous sodium bicarbonate and extracted with ethyl acetate (3×). Washed combined organics with saturated sodium chloride. Dried combined organics over magnesium sulfate, filtered, and evaporated. The crude reaction mixture was purified by column chromatography (DCM/MeOH) followed by RPLC (ACN/water) to afford N-(1,6-naphthyridin-2-yl)-2-(pyridine-4-yl)cyclopropane-1-carboxamide (S1-2, 53% yield). Trans racemic or trans-R,R compounds were prepared according to a similar procedure using the appropriate starting materials.

Using the general scheme shown above, making adjustments as necessary for protecting groups, etc., the compounds of Table 1 were synthesized.

TABLE 1

| Compound Number | Structure | $IC_{50}$ |
|---|---|---|
| 1 | 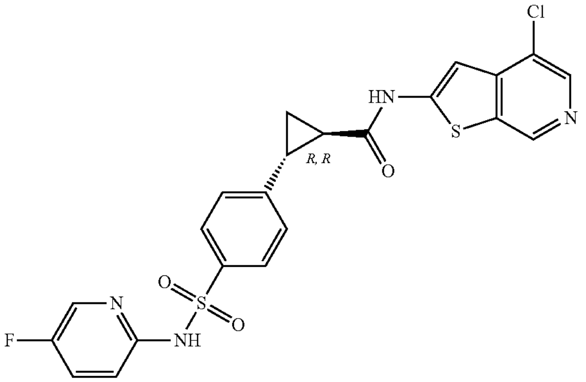 [SMILES: O=C(Nc1cc2c(Cl)cncc2s1)[C@@H]1C[C@H]1c1ccc(S(=O)(=O)Nc2ccc(F)cn2)cc1] | 12 nM JAK2 |
| 2 | 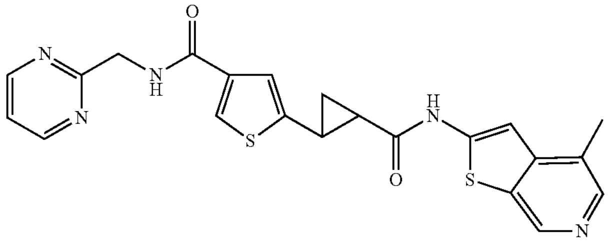 [SMILES: Cc1cncc2sc(NC(=O)C3CC3c3cc(C(=O)NCc4ncccn4)cs3)cc12] | 5.0 nM ROCK2 |
| 3 | 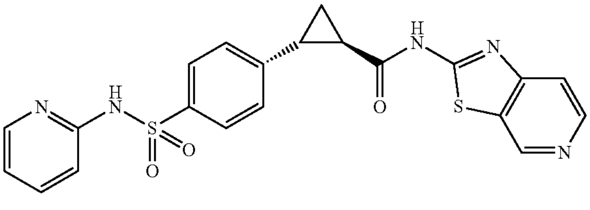<br>racemic | 6.0 nM ROCK2<br>7.0 nM ROCK1 |
| 4 | 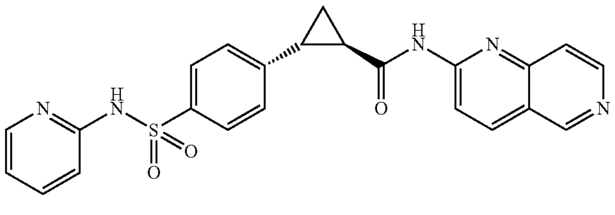<br>racemic | 22 nM JAK2<br>6.0 nM ROCK2 |

TABLE 1-continued
| Compound Number | Structure | $IC_{50}$ |
| --- | --- | --- |
| 5 | 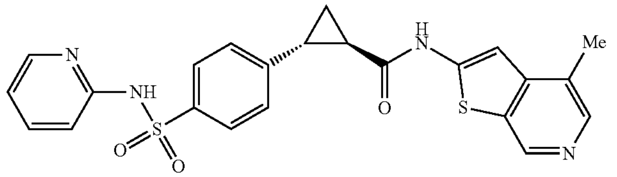 [SMILES: Cc1cncc2sc(NC(=O)[C@@H]3C[C@H]3c3ccc(S(=O)(=O)Nc4ccccn4)cc3)cc12] racemic | 8.9 nM JAK2 |
| 6 | 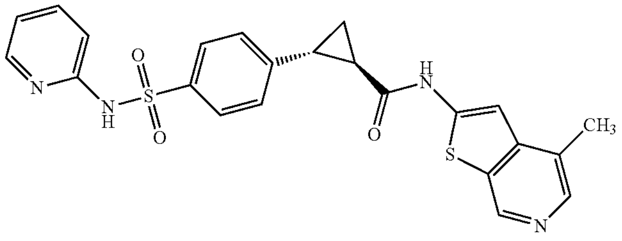 [SMILES: Cc1cncc2sc(NC(=O)[C@@H]3C[C@H]3c3ccc(S(=O)(=O)Nc4ccccn4)cc3)cc12] | 8.0 nM TYK2 |
| 7 | 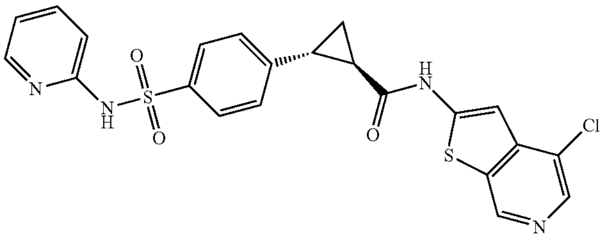 [SMILES: O=C(Nc1cc2c(Cl)cncc2s1)[C@@H]1C[C@H]1c1ccc(S(=O)(=O)Nc2ccccn2)cc1] | 1.1 nM TYK2 |
| 8 | 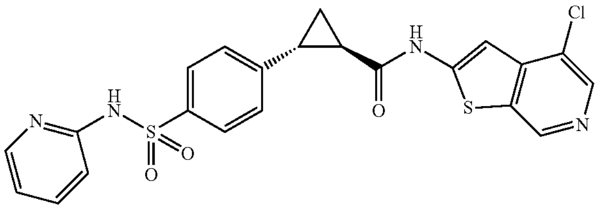 [SMILES: O=C(Nc1cc2c(Cl)cncc2s1)[C@@H]1C[C@H]1c1ccc(S(=O)(=O)Nc2ccccn2)cc1] | |
| 9 | 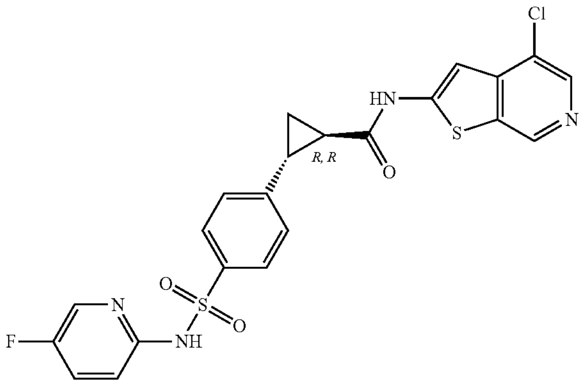 [SMILES: O=C(Nc1cc2c(Cl)cncc2s1)[C@@H]1C[C@H]1c1ccc(S(=O)(=O)Nc2ccc(F)cn2)cc1] | 12 nM JAK2 |
| 10 | 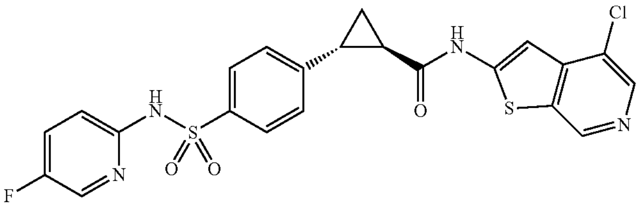 [SMILES: O=C(Nc1cc2c(Cl)cncc2s1)[C@@H]1C[C@H]1c1ccc(S(=O)(=O)Nc2ccc(F)cn2)cc1] | |

TABLE 1-continued
| Compound Number | Structure | $IC_{50}$ |
|---|---|---|
| 11 | 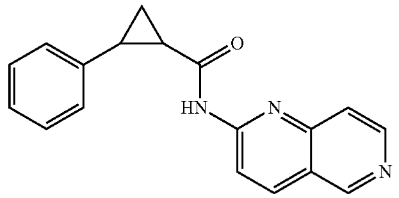 [SMILES: O=C(Nc1ccc2cnccc2n1)C1CC1c1ccccc1] | 7.0 nM ROCK2 |
| 12 | 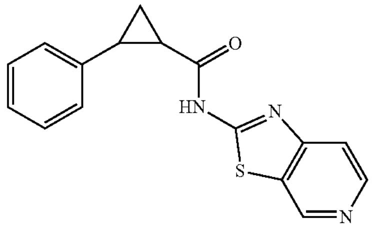 [SMILES: O=C(Nc1nc2ccncc2s1)C1CC1c1ccccc1] | 12 nM ROCK2 |
| 13 | 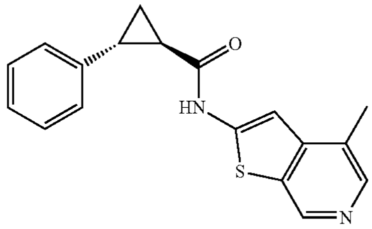 [SMILES: Cc1cncc2sc(NC(=O)[C@@H]3C[C@H]3c3ccccc3)cc12] | 18 nM ROCK2 |
| 14 | 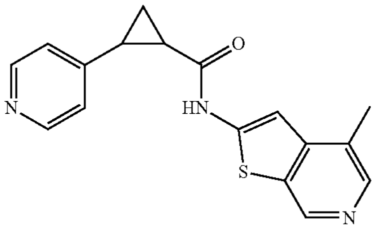 [SMILES: Cc1cncc2sc(NC(=O)C3CC3c3ccncc3)cc12] | 230 nM ROCK2 |
| 15 | 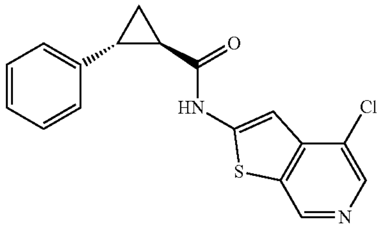 [SMILES: O=C(Nc1cc2c(Cl)cncc2s1)[C@@H]1C[C@H]1c1ccccc1] | 350 nM JAK1 |
| 16 | 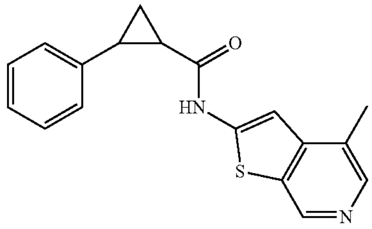 [SMILES: Cc1cncc2sc(NC(=O)C3CC3c3ccccc3)cc12] | 54 nM ROCK2 |

TABLE 1-continued
| Compound Number | Structure | $IC_{50}$ |
|---|---|---|
| 17 | 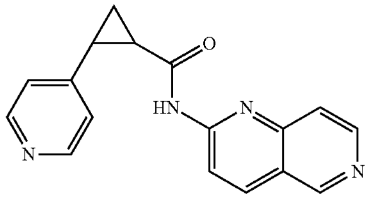 [SMILES: O=C(Nc1ccc2cnccc2n1)C1CC1c1ccncc1] | 30 nM ROCK2 |
| 18 | 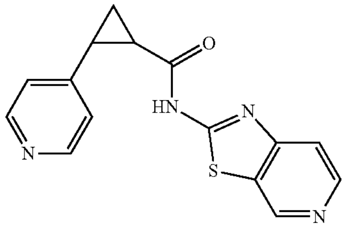 [SMILES: O=C(Nc1nc2ccncc2s1)C1CC1c1ccncc1] | 30 nM ROCK2 |
| 19 | 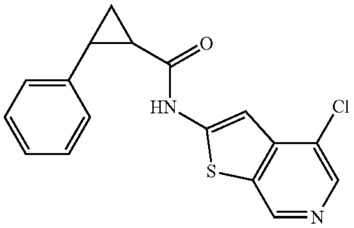 [SMILES: O=C(Nc1cc2c(Cl)cncc2s1)C1CC1c1ccccc1] | 43 nM ROCK1 |
| 20 | 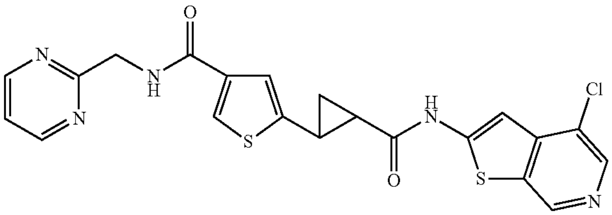 [SMILES: O=C(NCc1ncccn1)c1csc(C2CC2C(=O)Nc2cc3c(Cl)cncc3s2)c1] | 35 nM TYK2 |
| 21 | 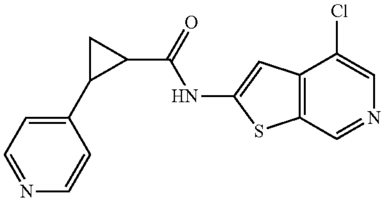 [SMILES: O=C(Nc1cc2c(Cl)cncc2s1)C1CC1c1ccncc1] | 111 nM ROCK2 |
| 22 | 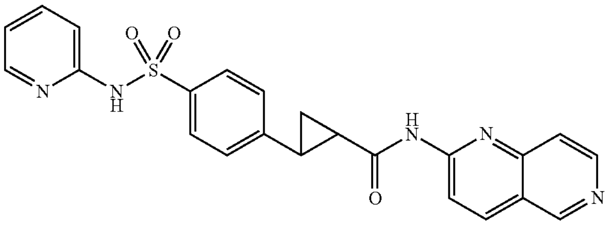 [SMILES: O=C(Nc1ccc2cnccc2n1)C1CC1c1ccc(S(=O)(=O)Nc2ccccn2)cc1] | 22 nM JAK2 |

Using a substantially the same procedures as described above, with appropriate modifications, compounds E26-E61 (Table 2) can be prepared.
TABLE 2
E26
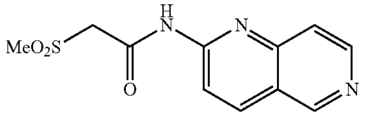 [SMILES: CS(=O)(=O)CC(=O)Nc1ccc2cnccc2n1]
E27
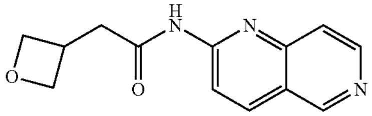 [SMILES: O=C(CC1COC1)Nc1ccc2cnccc2n1]
E28
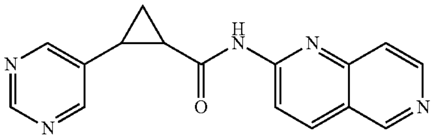 [SMILES: O=C(Nc1ccc2cnccc2n1)C1CC1c1cncnc1]
E29
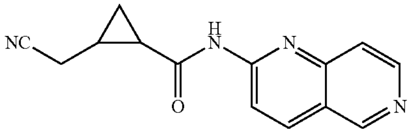 [SMILES: N#CCC1CC1C(=O)Nc1ccc2cnccc2n1]
E30
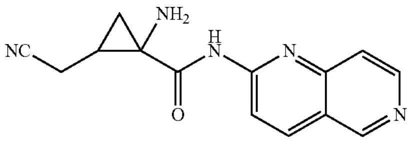 [SMILES: N#CCC1CC1(N)C(=O)Nc1ccc2cnccc2n1]
E31
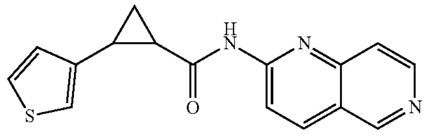 [SMILES: O=C(Nc1ccc2cnccc2n1)C1CC1c1ccsc1]
E32
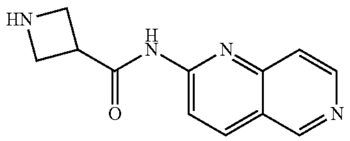 [SMILES: O=C(Nc1ccc2cnccc2n1)C1CNC1]
E33
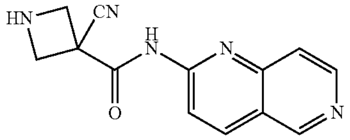 [SMILES: N#CC1(C(=O)Nc2ccc3cnccc3n2)CNC1]
E34
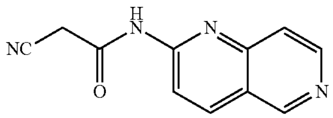 [SMILES: N#CCC(=O)Nc1ccc2cnccc2n1]
E35
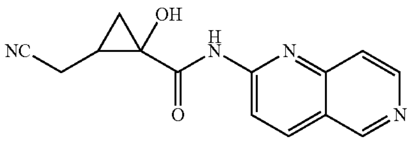 [SMILES: N#CCC1CC1(O)C(=O)Nc1ccc2cnccc2n1]
TABLE 2-continued
E36
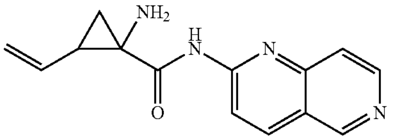 [SMILES: C=CC1CC1(N)C(=O)Nc1ccc2cnccc2n1]
E37
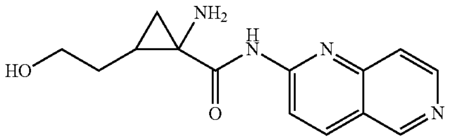 [SMILES: NC1(C(=O)Nc2ccc3cnccc3n2)CC1CCO]
E38
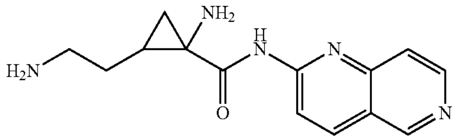 [SMILES: NCCC1CC1(N)C(=O)Nc1ccc2cnccc2n1]
E39
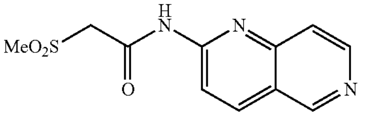 [SMILES: CS(=O)(=O)CC(=O)Nc1ccc2cnccc2n1]
E40
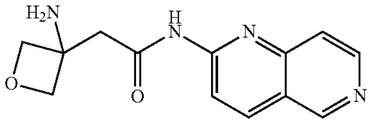 [SMILES: NC1(CC(=O)Nc2ccc3cnccc3n2)COC1]
E41
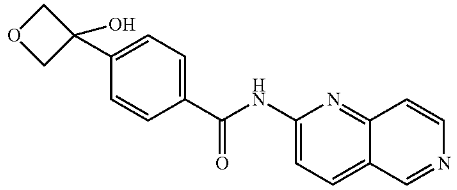 [SMILES: O=C(Nc1ccc2cnccc2n1)c1ccc(C2(O)COC2)cc1]
E42
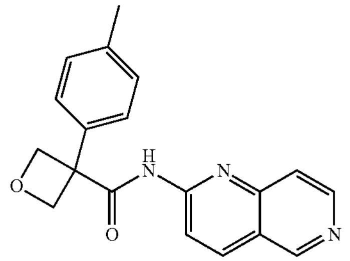 [SMILES: Cc1ccc(C2(C(=O)Nc3ccc4cnccc4n3)COC2)cc1]
E43
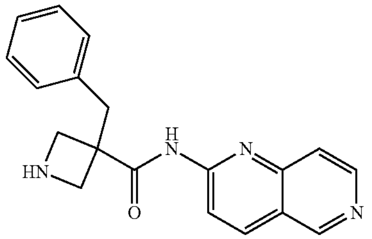 [SMILES: O=C(Nc1ccc2cnccc2n1)C1(Cc2ccccc2)CNC1]
E44
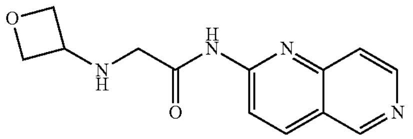 [SMILES: O=C(CNC1COC1)Nc1ccc2cnccc2n1]

TABLE 2-continued
| | |
|---|---|
| E45 | 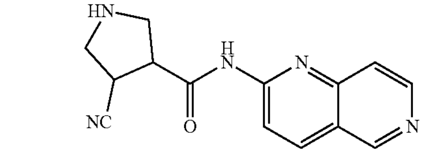 [SMILES: N#CC1CNCC1C(=O)Nc1ccc2cnccc2n1] |
| E46 | 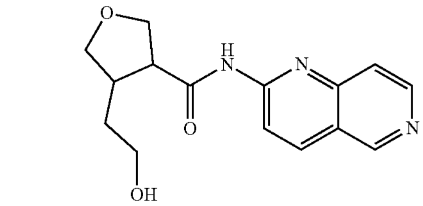 [SMILES: O=C(Nc1ccc2cnccc2n1)C1COCC1CCO] |
| E47 | 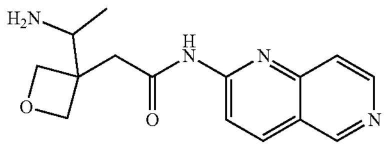 [SMILES: CC(N)C1(CC(=O)Nc2ccc3cnccc3n2)COC1] |
| E48 | 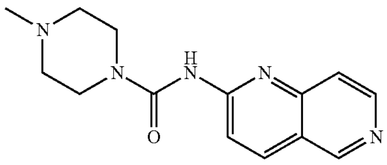 [SMILES: CN1CCN(C(=O)Nc2ccc3cnccc3n2)CC1] |
| E49 | 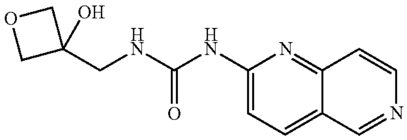 [SMILES: O=C(NCC1(O)COC1)Nc1ccc2cnccc2n1] |
| E50 | 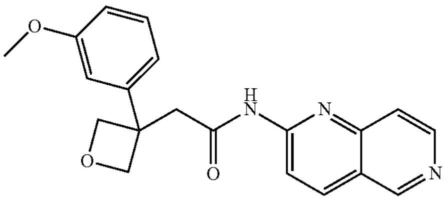 [SMILES: COc1cccc(C2(CC(=O)Nc3ccc4cnccc4n3)COC2)c1] |
| E51 | 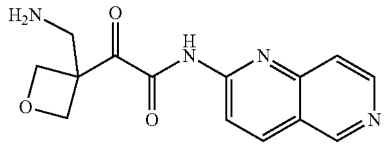 [SMILES: NCC1(C(=O)C(=O)Nc2ccc3cnccc3n2)COC1] |
| E52 | 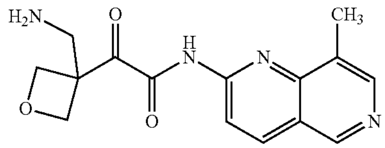 [SMILES: Cc1cncc2ccc(NC(=O)C(=O)C3(CN)COC3)nc12] |
| E53 | 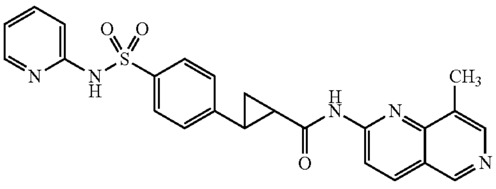 [SMILES: Cc1cncc2ccc(NC(=O)C3CC3c3ccc(S(=O)(=O)Nc4ccccn4)cc3)nc12] |
TABLE 2-continued
| | |
|---|---|
| E54 | 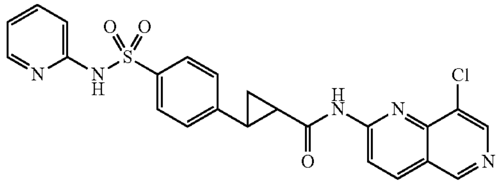 [SMILES: O=C(Nc1ccc2cncc(Cl)c2n1)C1CC1c1ccc(S(=O)(=O)Nc2ccccn2)cc1] |
| E55 | 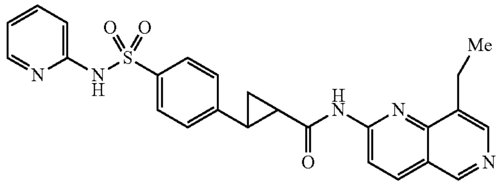 [SMILES: CCc1cncc2ccc(NC(=O)C3CC3c3ccc(S(=O)(=O)Nc4ccccn4)cc3)nc12] |
| E56 | 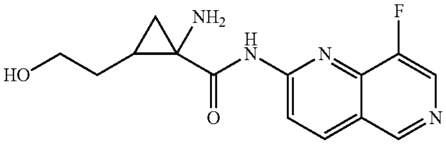 [SMILES: NC1(C(=O)Nc2ccc3cncc(F)c3n2)CC1CCO] |
| E57 | 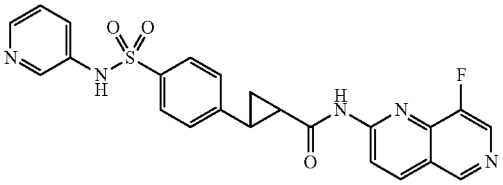 [SMILES: O=C(Nc1ccc2cncc(F)c2n1)C1CC1c1ccc(S(=O)(=O)Nc2cccnc2)cc1] |
| E58 | 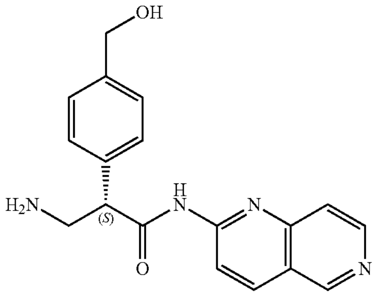 |
| E59 | 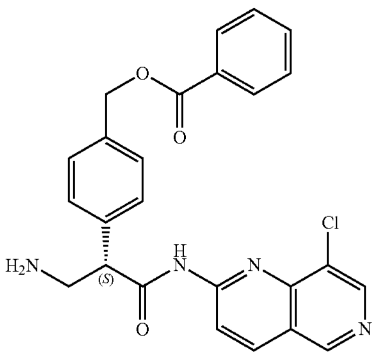 |

TABLE 2-continued

E60

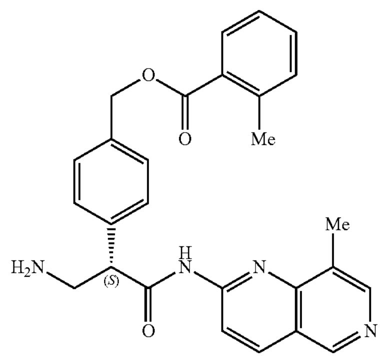

E61

Scheme 2.

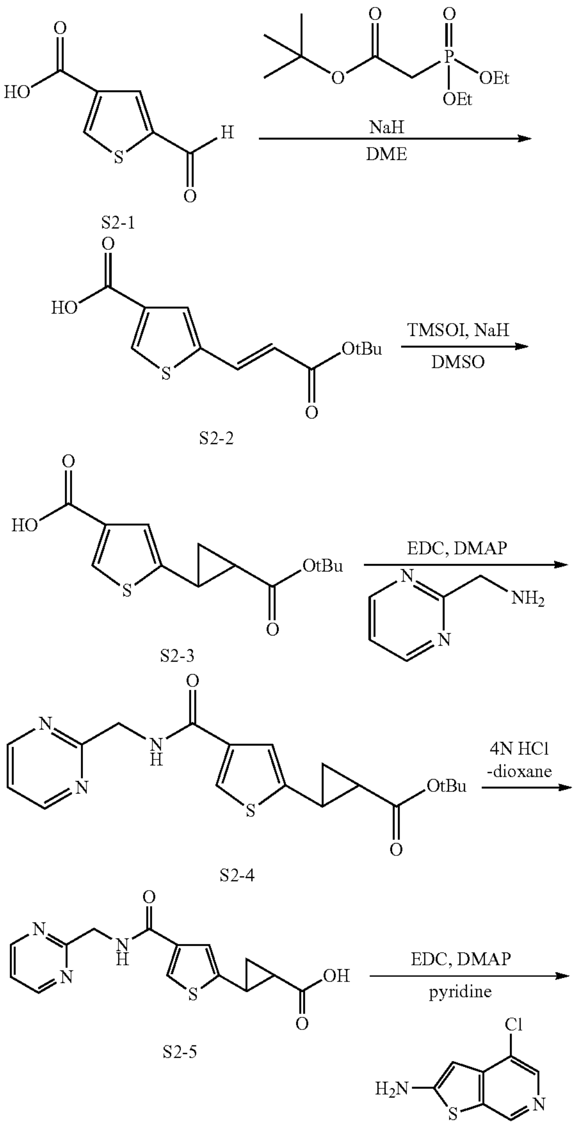

S2-1

S2-2

S2-3

S2-4

S2-5

-continued

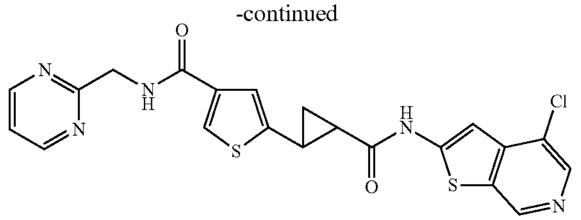

S2-6

(E)-5-(3-(tert-butoxy)-3-oxoprop-1-en-1-yl)thiophene-3-carboxylic acid (S2-2). To 5-formylthiophene-3-carboxylic acid in DME at 0° C. was added tert-butyl 2-(diethoxyphosphoryl)acetate and NaH and solution was warmed to room temperature then heated at 30° C. After 3 hours the reaction is poured into EtOAc and HCl (1N), extracted, dried ($Na_2SO_4$) filtered and evaporated to give crude 2. Column chromatography (0-20% EtOAc-Hexanes) gave pure (E)-5-(3-(tert-butoxy)-3-oxoprop-1-en-1-yl) thiophene-3-carboxylic acid (S2-2, 82%).

5-(2-(tert-butoxycarbonyl)cyclopropyl)thiophene-3-carboxylic acid (S2-3). To TMSOI in DMSO was added NaH and solution was stirred for 1 hour at room temperature. Then (E)-5-(3-(tert-butoxy)-3-oxoprop-1-en-1-yl)thiophene-3-carboxylic acid (S2-2) in DMSO was added and solution stirred at 30° C. for 1-3 hours. The mixture was cooled and poured into cold EtOAc-HCl(1N) and extracted, dried ($Na_2SO_4$) filtered and evaporated. Column chromatography 5% MeOH—$CH_2Cl_2$ gave pure 5-(2-(tert-butoxycarbonyl)cyclopropyl)thiophene-3-carboxylic acid (73%, S2-3).

tert-Butyl-2-(4-((pyrimidin-2-ylmethyl)carbamoyl)thiophen-2-yl)cyclopropane-1-carboxylate (S2-4). To 5-(2-(tert-butoxycarbonyl)cyclopropyl)thiophene-3-carboxylic acid (S2-3) in pyridine was added EDC, DMAP and pyrimidin-2-ylmethanamine hydrochloride and solution was stirred at room temperature overnight. The mixture was poured into EtOAc-$NaHCO_3$ (sat) and extracted, dried ($Na_2SO_4$), filtered and evaporated. Column chromatography (0-5%) MeOH—$CH_2Cl_2$ gave pure tert-butyl 2-(4-((pyrimidin-2-ylmethyl)carbamoyl)thiophen-2-yl)cyclopropane-1-carboxylate (97%, S2-4)

2-(4-((pyrimidin-2-ylmethyl)carbamoyl)thiophen-2-yl) cyclopropane-1-carboxylic acid (S2-5). To tert-butyl 2-(4-((pyrimidin-2-ylmethyl)carbamoyl)thiophen-2-yl)cyclopropane-1-carboxylate (S2-4) in $CH_2Cl_2$ was added HCl (4N) and solution was stirred overnight. The $CH_2Cl_2$ was decanted off and the compound was washed with $Et_2O$, dried to give 2-(4-((pyrimidin-2-ylmethyl)carbamoyl)thiophen-2-yl)cyclopropane-1-carboxylic acid hydrochloride (S2-5). (>90%)

5-(2-((4-chlorothieno[2,3-c]pyridin-2-yl)carbamoyl)cyclopropyl)-N-(pyrimidin-2-ylmethyl)thiophene-3-carboxamide (S2-6). To 2-(4-((pyrimidin-2-ylmethyl)carbamoyl) thiophen-2-yl)cyclopropane-1-carboxylic acid hydrochloride (S2-5) in pyridine was added EDC, DMAP and 2-(λ2-azanyl)-4-chlorothieno[2,3-c]pyridine and the solution was stirred at room temperature overnight. The reaction was poured into EtOAc-$NaHCO_3$(sat) extracted, dried ($Na_2SO_4$) filtered and evaporated. Column chromatography to give 5-(2-((4-chlorothieno[2,3-c]pyridin-2-yl) carbamoyl)cyclopropyl)-N-(pyrimidin-2-ylmethyl)thiophene-3-carboxamide (48%, S2-6).

Using procedures similar to those set forth above for Scheme 1 and substituting the appropriate starting materials, the compounds E107-119 (Table 3) were made and E120-146 (Table 4) could be synthesized.
TABLE 3
E107
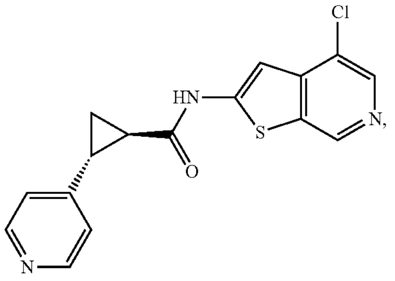 [SMILES: O=C(Nc1cc2c(Cl)cncc2s1)[C@@H]1C[C@H]1c1ccncc1]
trans racemic
E108
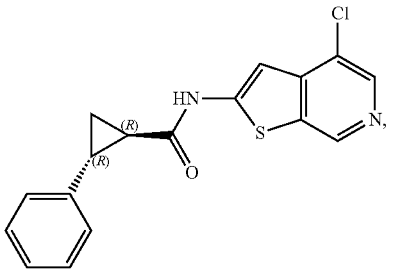
R,R enantiomer
E109
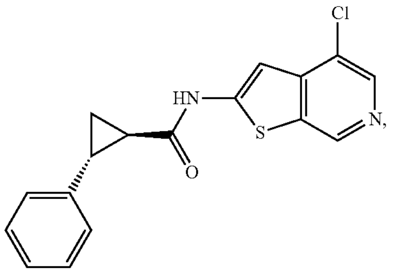 [SMILES: O=C(Nc1cc2c(Cl)cncc2s1)[C@@H]1C[C@H]1c1ccccc1]
trans racemic
E110
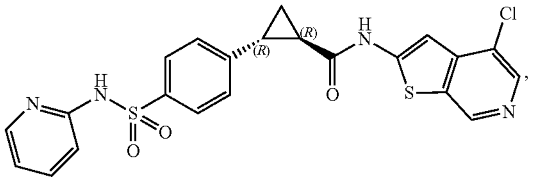
R,R enantiomer
E111
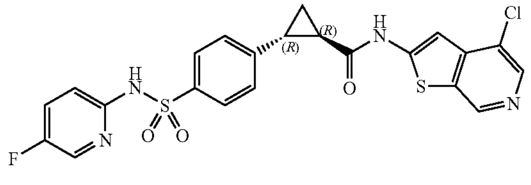
R,R enantiomer
TABLE 3-continued
E112
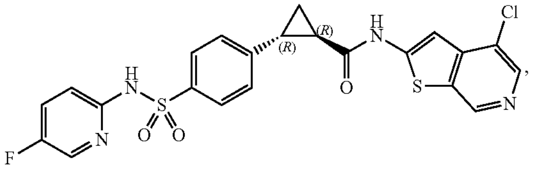
R,R enantiomer
E113
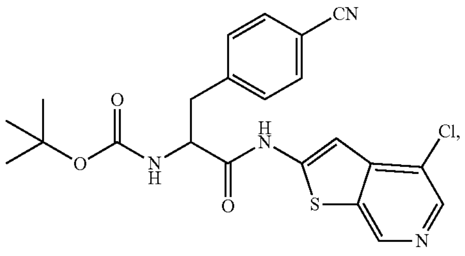 [SMILES: CC(C)(C)OC(=O)NC(Cc1ccc(C#N)cc1)C(=O)Nc1cc2c(Cl)cncc2s1]
R,R enantiomer
E114
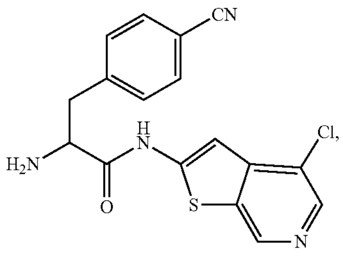 [SMILES: N#Cc1ccc(CC(N)C(=O)Nc2cc3c(Cl)cncc3s2)cc1]
R,R enantiomer
E115
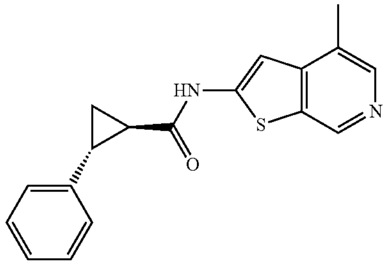 [SMILES: Cc1cncc2sc(NC(=O)[C@@H]3C[C@H]3c3ccccc3)cc12]
trans racemic
E116
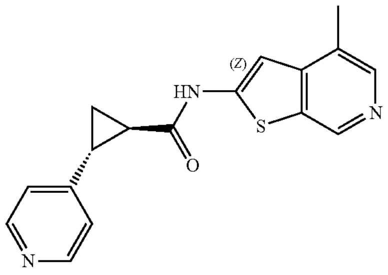 [SMILES: Cc1cncc2sc(NC(=O)[C@@H]3C[C@H]3c3ccncc3)cc12]
trans racemic TABLE 3-continued
E116
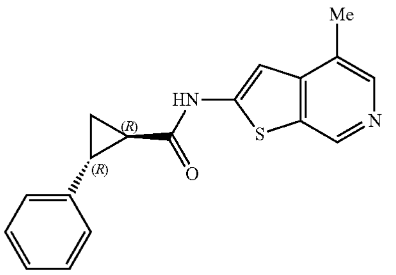
R,R enantiomer
E117
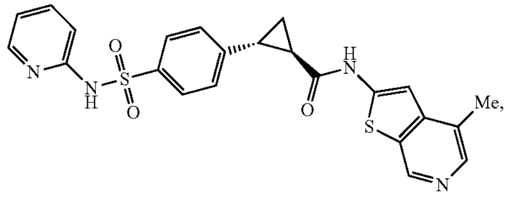 [SMILES: Cc1cncc2sc(NC(=O)[C@@H]3C[C@H]3c3ccc(S(=O)(=O)Nc4ccccn4)cc3)cc12]
trans racemic
E118
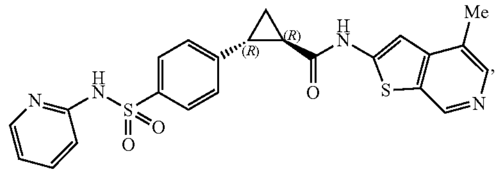
R,R enantiomer
E119
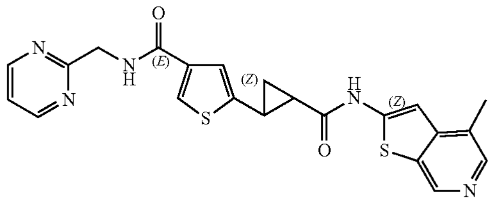 [SMILES: Cc1cncc2sc(NC(=O)C3CC3c3cc(C(=O)NCc4ncccn4)cs3)cc12]
trans racemic
TABLE 4
E120
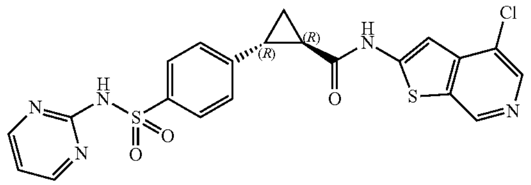
E121
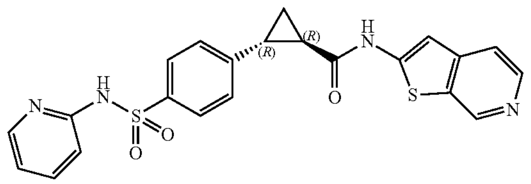
TABLE 4-continued
E122
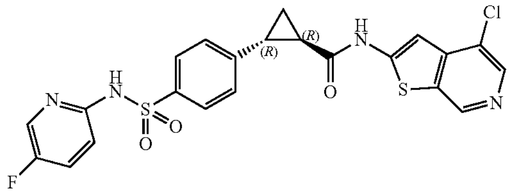
E123
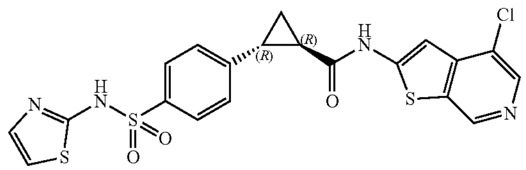
E124
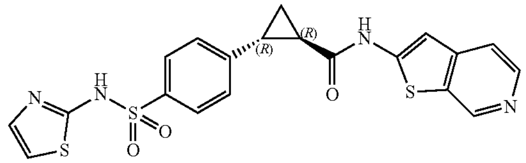
E125
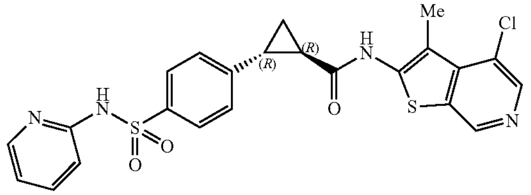
E126
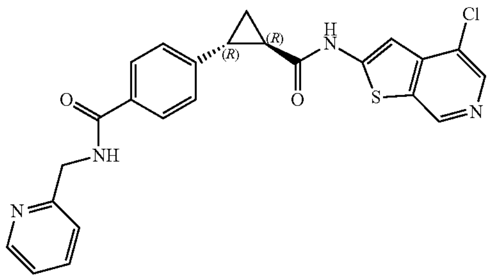
E127
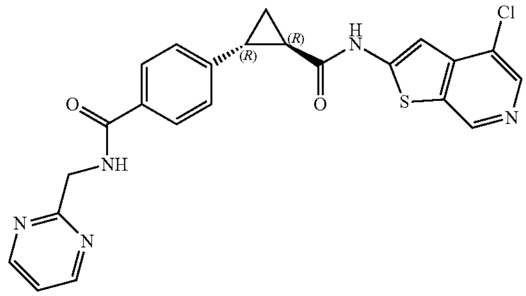
E128
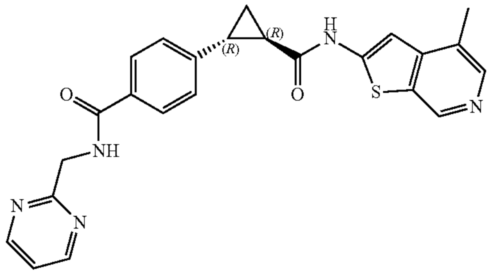

TABLE 4-continued
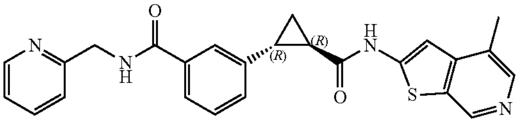
E129
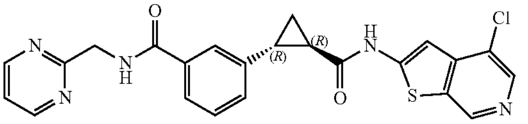
E130
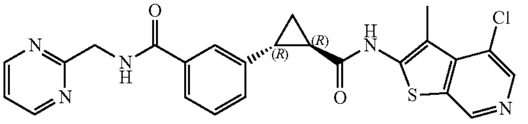
E131
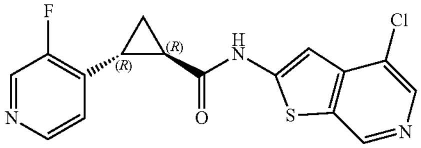
E132
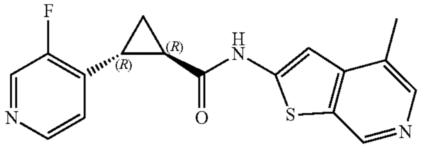
E133
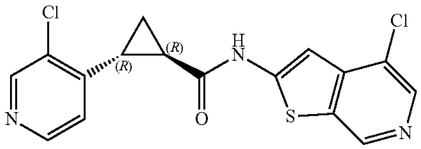
E134
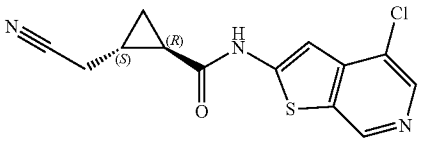
E135
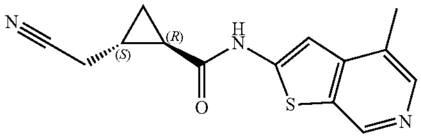
E136
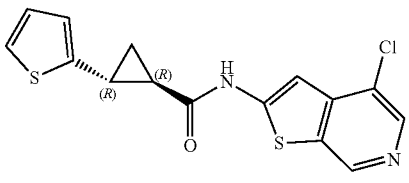
E137
TABLE 4-continued
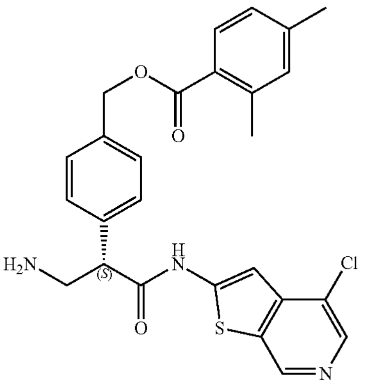
E138
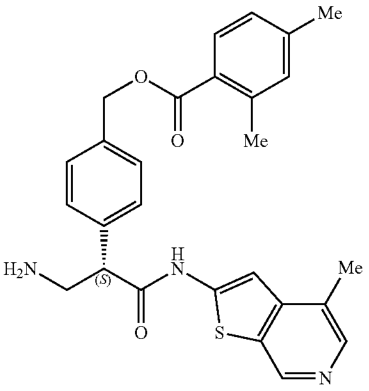
E139
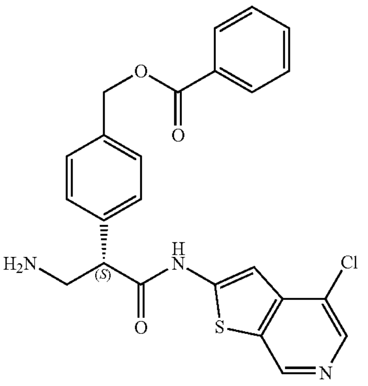
E140
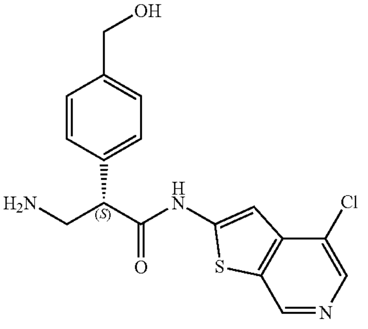
E141

TABLE 4-continued

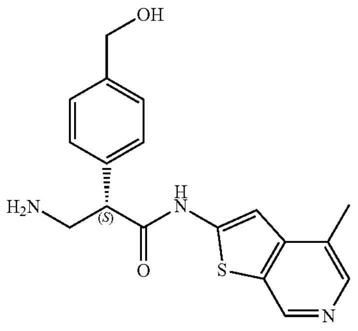

E142

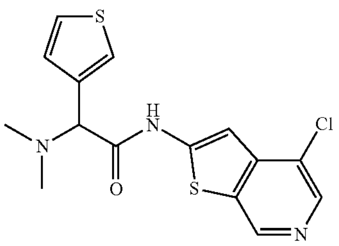 [SMILES: CN(C)C(C(=O)Nc1cc2c(Cl)cncc2s1)c1ccsc1]

E143

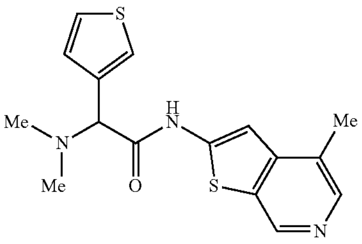 [SMILES: Cc1cncc2sc(NC(=O)C(c3ccsc3)N(C)C)cc12]

E144

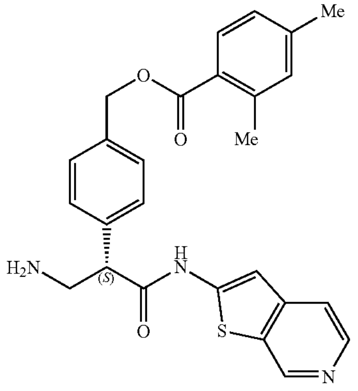

E145

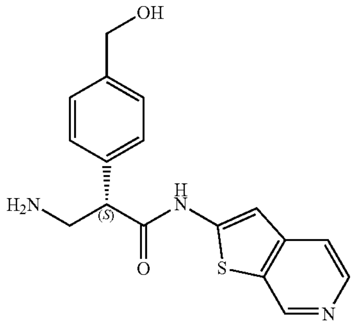

E146

Scheme 3

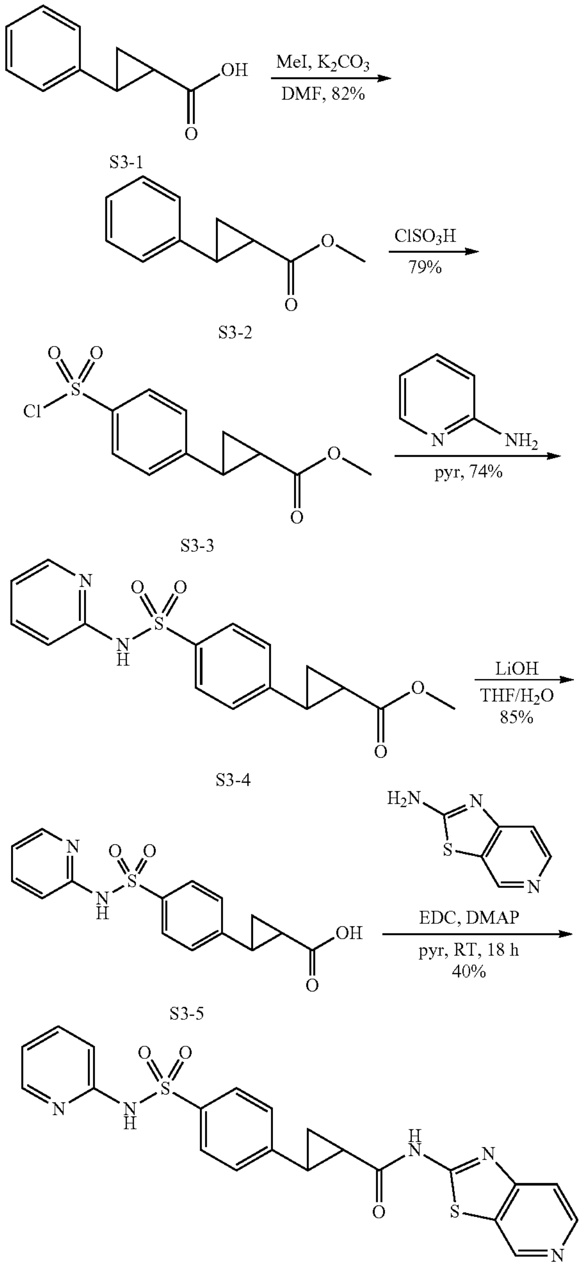

Preparation of methyl 2-phenylcyclopropane-1-carboxylate (S3-2)

To a solution of 2-phenylcyclopropane-1-carboxylic acid (S3-1) in anhydrous DMF at 0° C. was added $K_2CO_3$, then methyl iodide. Reaction was stirred at room temperature for 3 hours or until complete by TLC. The mixture was poured over sat $NaHCO_3$ and extracted with EtOAc. The organic layer was washed with brine and then dried over $Na_2SO_4$, filtered and concentrated under reduced vacuum. Column chromatography 0-10% hex/EtOAc gave methyl 2-phenyl-cyclopropane-1-carboxylate as a clear, colorless oil (S3-2, 82%).

Preparation of methyl 2-(4-(chlorosulfonyl)phenyl) cyclopropane-1-carboxylate (S3-3)

To chlorosulfonic acid at 0° C. was added neat methyl 2-phenylcyclopropane-1-carboxylate (S3-2) dropwise over 15 minutes. The reaction was stirred for 3 hours or until complete by TLC. The mixture was poured over ice water and extracted with EtOAc. The organic layer was washed with brine and then dried over $Na_2SO_4$, filtered and concentrated under reduced vacuum. Column chromatography 0-15% hex/EtOAc gave methyl 2-(4-(chlorosulfonyl)phenyl)cyclopropane-1-carboxylate as a white solid (S3-3, 79%).

Preparation of methyl 2-(4-(N-(pyridin-2-yl)sulfamoyl)phenyl)cyclopropane-1-carboxylate (S3-4)

To a solution of methyl 2-(4-(chlorosulfonyl)phenyl)cyclopropane-1-carboxylate (3) in anhydrous pyridine at 0° C. was added pyridin-2-amine. The reaction was stirred for 1 hour or until complete by TLC. The mixture was poured over sat $NaHCO_3$ and extracted with EtOAc. The organic layer was washed with brine and then dried over $Na_2SO_4$, filtered and concentrated under reduced vacuum. Column chromatography 0-5% $MeOH/CH_2Cl_2$ gave methyl 2-(4-(N-(pyridin-2-yl)sulfamoyl)phenyl)cyclopropane-1-carboxylate as a white solid (S3-4, 74%).

Preparation of 2-(4-(N-(pyridin-2-yl)sulfamoyl)phenyl)cyclopropane-1-carboxylic acid (S3-5)

To a solution of 2-(4-(N-(pyridin-2-yl)sulfamoyl)phenyl) cyclopropane-1-carboxylate (S3-4) in $THF/H_2O$ was added $LiOH{\cdot}H_2O$ and the solution was stirred for 6 hours. The pH was adjusted to 5 with HCl (1N). The aqueous layer was extracted with EtOAc, dried ($Na_2SO_4$), filtered and evaporated to give 2-(4-(N-(pyridin-2-yl)sulfamoyl)phenyl)cyclopropane-1-carboxylic acid as a white solid (S3-5, 85%).

Preparation of 2-(4-(N-(pyridin-2-yl)sulfamoyl)phenyl)-N-(thiazolo[5,4-c]pyridin-2-yl)cyclopropane-1-carboxamide (S3-6)

To a solution of 2-(4-(N-(pyridin-2-yl)sulfamoyl)phenyl) cyclopropane-1-carboxylic acid (S3-5) in anhydrous pyridine was added EDC, DMAP and thiazolo[5,4-c]pyridin-2-amine and the solution was stirred under $N_2$ overnight. The reaction mixture was concentrated. Column chromatography 0-5% $MeOH/CH_2Cl_2$ gave pure 2-(4-(N-(pyridin-2-yl) sulfamoyl)phenyl)-N-(thiazolo[5,4-c]pyridin-2-yl)cyclopropane-1-carboxamide (S3-6, 40%).

Using procedures similar to those set forth above for Scheme 3 and substituting the appropriate starting materials, the compounds E201-E203 (Table 5) were made and E204-218 (Table 6) could be synthesized.

TABLE 5

E201

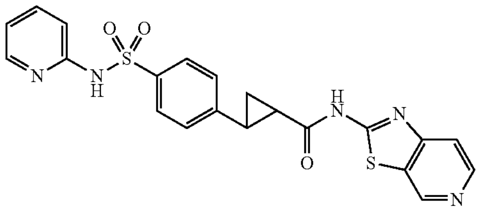

TABLE 5-continued

E202

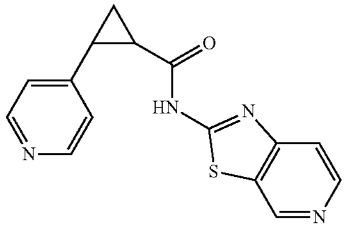 [SMILES: O=C(Nc1nc2ccncc2s1)C1CC1c1ccncc1]

E203

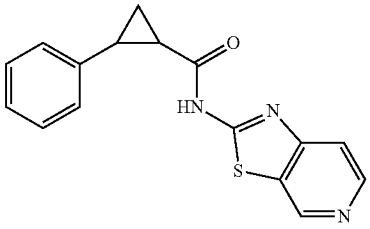 [SMILES: O=C(Nc1nc2ccncc2s1)C1CC1c1ccccc1]

TABLE 6

E204

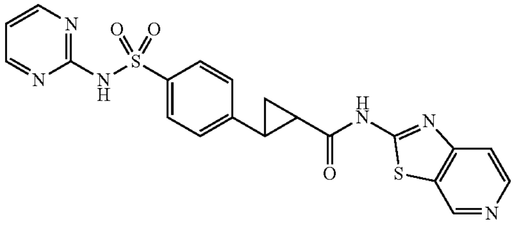 [SMILES: O=C(Nc1nc2ccncc2s1)C1CC1c1ccc(S(=O)(=O)Nc2ncccn2)cc1]

E205

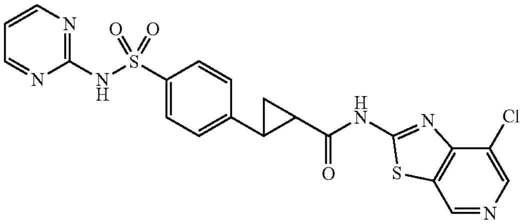 [SMILES: O=C(Nc1nc2c(Cl)cncc2s1)C1CC1c1ccc(S(=O)(=O)Nc2ncccn2)cc1]

E206

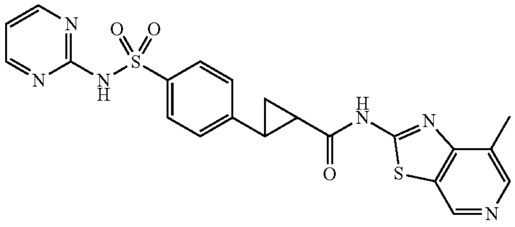 [SMILES: Cc1cncc2sc(NC(=O)C3CC3c3ccc(S(=O)(=O)Nc4ncccn4)cc3)nc12]

E207

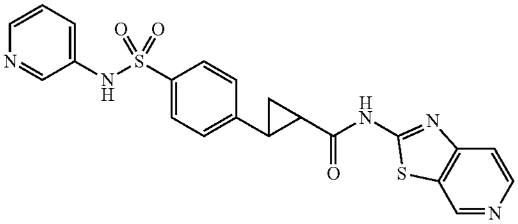 [SMILES: O=C(Nc1nc2ccncc2s1)C1CC1c1ccc(S(=O)(=O)Nc2cccnc2)cc1]

TABLE 6-continued
E208
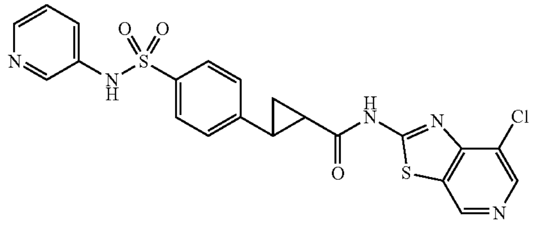 [SMILES: O=C(Nc1nc2c(Cl)cncc2s1)C1CC1c1ccc(S(=O)(=O)Nc2cccnc2)cc1]
E209
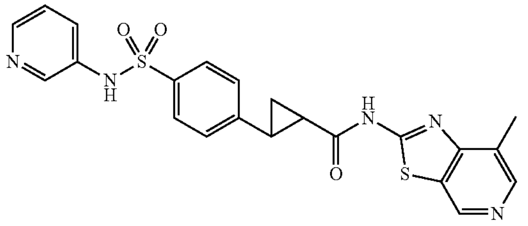 [SMILES: Cc1cncc2sc(NC(=O)C3CC3c3ccc(S(=O)(=O)Nc4cccnc4)cc3)nc12]
E210
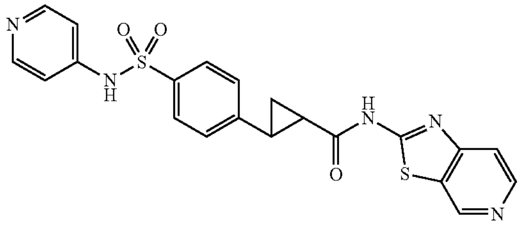
E211
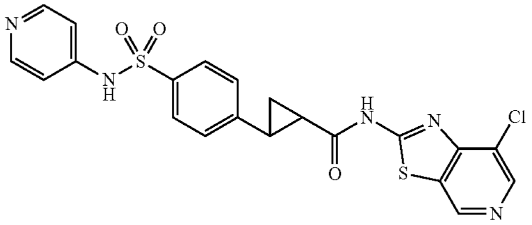 [SMILES: O=C(Nc1nc2c(Cl)cncc2s1)C1CC1c1ccc(S(=O)(=O)Nc2ccncc2)cc1]
E212
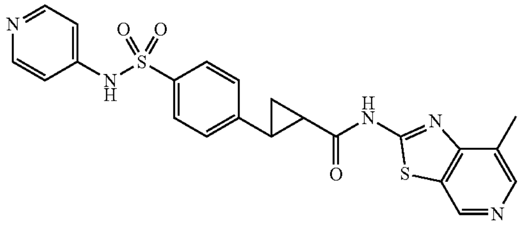 [SMILES: Cc1cncc2sc(NC(=O)C3CC3c3ccc(S(=O)(=O)Nc4ccncc4)cc3)nc12]
E213
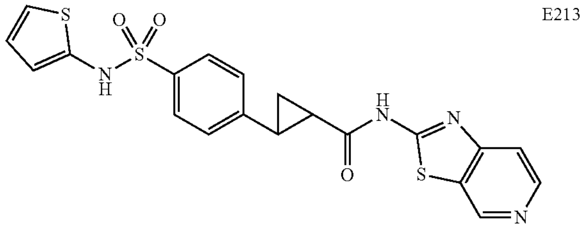
E214
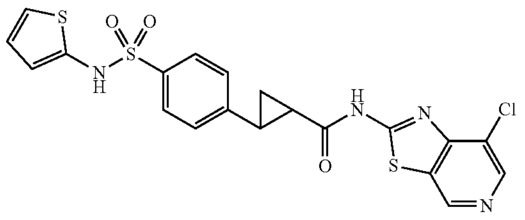 [SMILES: O=C(Nc1nc2c(Cl)cncc2s1)C1CC1c1ccc(S(=O)(=O)Nc2cccs2)cc1]
TABLE 6-continued
E215
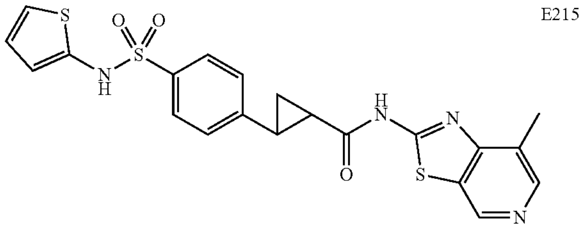
E216
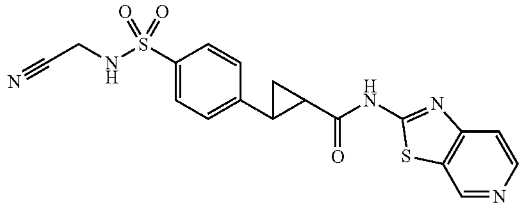 [SMILES: N#CCNS(=O)(=O)c1ccc(C2CC2C(=O)Nc2nc3ccncc3s2)cc1]
E217
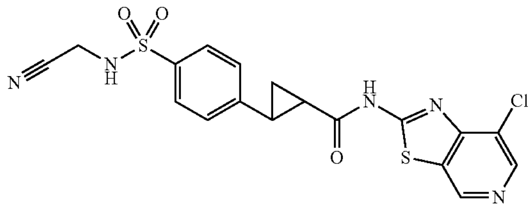 [SMILES: N#CCNS(=O)(=O)c1ccc(C2CC2C(=O)Nc2nc3c(Cl)cncc3s2)cc1]
E218
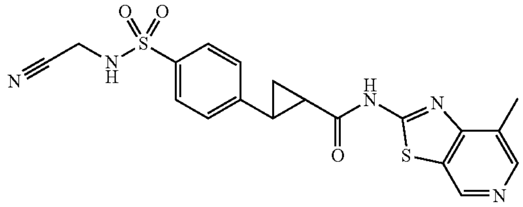 [SMILES: Cc1cncc2sc(NC(=O)C3CC3c3ccc(S(=O)(=O)NCC#N)cc3)nc12]
E219
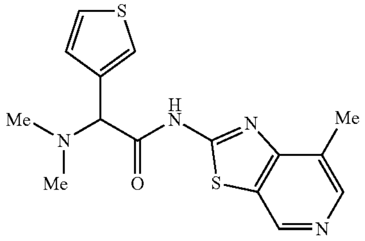 [SMILES: Cc1cncc2sc(NC(=O)C(c3ccsc3)N(C)C)nc12]
E220
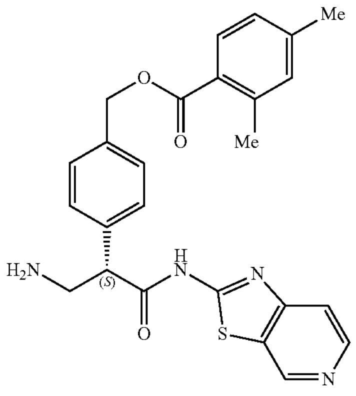

TABLE 6-continued

E221

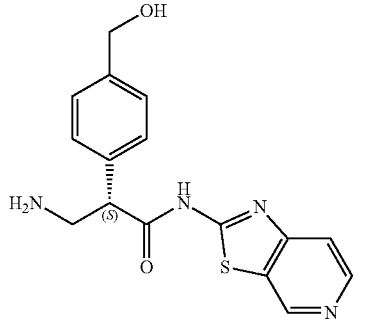

E222

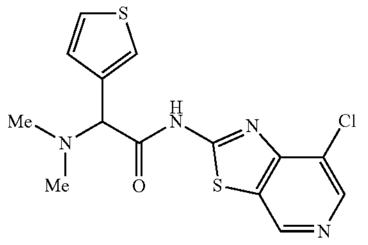 [SMILES: CN(C)C(C(=O)Nc1nc2c(Cl)cncc2s1)c1ccsc1]

E223

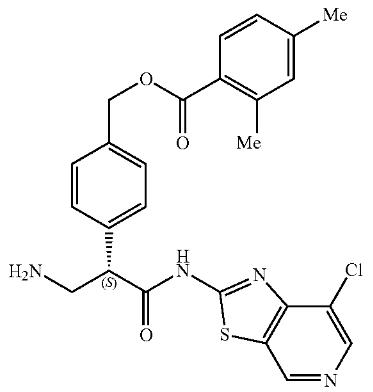

E224

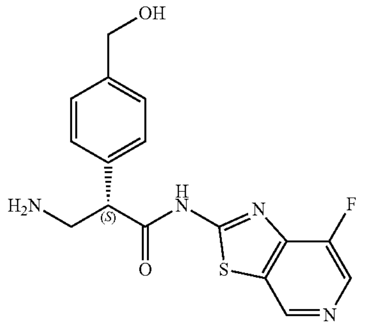

Isomers

Compounds described herein may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral chromatography column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/ enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Salts

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci.* Vol. 66, pp. 1-19. In an embodiment, the compound is present in mono-salt form. In embodiments, the compound is present in di-salt form.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, triethylamine, butylamine, ethylenediamine, ethanolamine, diethanolamine, piperazine, benzylamine, phenylbenzylamine, choline, meglumine, and tromethamine, as well as dibasic amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, p-toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxyl group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—$OC(O)CH_3$, —OAc).

An aldehyde or ketone group may be protected as an acetal ($RCH(OR)_2$) or ketal ($R_2C(OR)_2$), respectively, in which the carbonyl group ($R_2C{=}O$) is converted to a diether ($R_2C(OR)_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—$NHC(O)CH_3$); a benzyloxy amide (—$NHC(O)OCH_2C_6H_5$, —NH-Cbz); as a tert-butoxy amide (—$NHC(O)OC(CH_3)_3$, —NH-Boc); a 2-biphenyl-2-propoxy amide (—$NHCO(O)C(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—$CH_2NHC(O)CH_3$)

Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. Prodrugs can be converted to the compounds of the present disclosure by chemical or biochemical methods in an ex vivo environment. For example, prodrugs can be slowly converted to the compounds of the present disclosure when placed in a transdermal patch reservoir with or without a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Synthesis

Methods of synthesizing the herein described compounds will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Methods of Use and Activity

The compounds as disclosed herein and compositions including them have kinase inhibitory activity and are thus useful in modulating the action of kinases, and in treatment and/or prevention of diseases or conditions influenced by kinases. The above compounds and compositions may be used to modulate (e.g., influence or inhibit) the action of kinases either in a cell in vitro or in a cell in a living body in vivo. Specifically, in one embodiment, a method is provided of inhibiting the action of a kinase comprising applying to a medium such as an assay medium or contacting with a cell either in a cell in vitro or in a cell in a living body in vivo an effective inhibitory amount of a compound as disclosed herein. In one embodiment, the kinase inhibited is a rho kinase (e.g., ROCK1 or ROCK2). In another embodiment, the kinase inhibited is a JAK (e.g., JAK2) kinase.

JAK inhibitors are useful in treating various JAK-associated diseases or disorders. Examples of JAK-associated diseases include diseases involving the immune system including, for example, organ transplant rejection (e.g., allograft rejection and graft versus host disease). Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is arthritis.

Further examples of JAK-associated diseases include allergic conditions such as asthma, food allergies, eczematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides. Other examples of JAK-associated diseases or conditions include pulmonary arterial hypertension.

Other examples of JAK-associated diseases or conditions include inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer. All of these indications are also indications for ROCK inhibitiors.

The compounds of the present disclosure are used in methods of inhibiting kinases in a cell, a tissue or a subject such as a human comprising contacting the cell with an amount of one or more of the compounds of the present disclosure effective to inhibit the kinase. In one embodiment, the compounds are administered in a pharmaceutically acceptable composition, such as in or with a pharmaceutically acceptable carrier.

In another embodiment, the compounds of the present disclosure are used in methods for modulating the action of a kinase in a cell comprising contacting the cell with amount of one or more compounds of the present disclosure effective to modulate the action of a kinase in a cell. In one embodiment, the compounds of the present disclosure are administered in a pharmaceutically acceptable composition, such as in or with a pharmaceutically acceptable carrier.

Treatment or prevention of diseases or conditions for which the compounds of the present disclosure may be useful includes any of the diseases or conditions associated with kinase activity or diseases or conditions affected by kinases. Examples of these types of diseases include neurodegenerative diseases, such as Alzheimer's; ocular diseases, such as diabetic eye diseases, wet age-related macular degeneration, or dry age-related macular degeneration, inflammatory eye diseases, retinal degradation and glaucoma; cardiovascular diseases; and cancer. Additional examples include bone disorder, obesity, hepatic disease, renal disease, pancreatitis, gastric disturbance, hypertension, fertility control, disorders of hair growth, nasal congestion, neurogenic bladder disorder, gastrointestinal disorder, dermatological disorder, and respiratory indications.

In some embodiments, the compounds of the present disclosure will be administered in conjunction with one or more additional therapeutic agents. Suitable classes of additional therapeutic agents include, but are not limited to, beta blockers, alpha-agonists, carbonic anhydrase inhibitors, prostaglandin-like compounds, miotic or cholinergic agents, epinephrine compounds, or neuroprotective or anti-inflammatory compounds.

Beta blockers. These compounds are thought to lower intraocular pressure (IOP) by reducing the production of aqueous humor. Examples include levobunolol (BETAGAN™), timolol (BETIMOL™, TIMOPTIC™), betaxolol (BETOPTIC™) and metipranolol (OPTIPRANOLOL™).

Alpha-agonists. These compounds are thought to lower IOP by reducing the production of aqueous humor and increasing drainage. Examples include apraclonidine (IOPIDINE™) and brimonidine (ALPHAGAN™).

Carbonic anhydrase inhibitors. These compounds are thought to lower IOP by also reducing the production of aqueous humor. Examples include dorzolamide (TRUSOPT™) and brinzolamide (AZOPT™).

Prostaglandin-like compounds. These compounds are thought to lower IOP by increasing the outflow of aqueous humor by the uveoscleral pathway. Examples include AR-102, latanoprost (XALATAN™), bimatoprost (LUMIGAN™), tafluprost (ZIOPTAN™), and travoprost (TRAVATAN™).

Miotic or cholinergic agents. These agents are thought to function by causing the pupil to constrict, which opens drainage channels in the eye. Examples include pilocarpine (ISOPTO CARPINE™, PILOPINE™) and carbachol (ISOPTO CARBACHOL™).

Epinephrine compounds. These compounds, such as dipivefrin (PROPINE™), are thought to function by both decreasing the outflow of aqueous humor, as well as increasing fluid drainage.

Neuroprotective or anti-inflammatory compounds. These compounds, such as Aflibercept (EYLEA™) are treatments for conditions of the retina such as Macular Degeneration, and are designed as anti-VEGF treatments or have similar types of anti-growth or anti-inflammatory activity.

Thus, provided herein are methods of treating an ocular disorder in a subject in need thereof, comprising administering to the subject a compound, a composition, or a pharmaceutical composition provided herein.

Also provided herein are methods of reducing intraocular pressure in a subject in need thereof, comprising administering to the subject a compound, a composition, or a pharmaceutical composition provided herein.

In one aspect, provided herein are methods of treating an ocular disorder in a subject in need thereof, comprising administering to the subject a compound, or a pharmaceutically acceptable salt thereof, provided herein.

In some embodiments, the ocular disorder is glaucoma.

In another aspect, provided herein are methods of reducing intraocular pressure in a subject in need thereof, comprising administering to the subject a compound, or a pharmaceutically acceptable salt thereof, provided herein.

In some embodiments of these aspects, the compound is administered topically to an eye of the subject.

In some embodiments, provided herein are methods of treating an ocular disorder in a subject in need thereof, comprising administering to the subject a compound of one of the Formulae provided herein, or a pharmaceutically acceptable salt thereof.

In some embodiments, provided herein are methods of treating an ocular disorder in a subject in need thereof, comprising administering to the subject a compound provided in Table 1, or a pharmaceutically acceptable salt thereof.

In some embodiments, provided herein are methods of reducing intraocular pressure in a subject in need thereof, comprising administering to the subject a compound of one of the Formulae provided herein, or a pharmaceutically acceptable salt thereof.

In some embodiments, provided herein are methods of reducing intraocular pressure in a subject in need thereof, comprising administering to the subject a compound provided in Table 1, or a pharmaceutically acceptable salt thereof.

In some embodiments of these methods, the method further comprises administering one or more additional therapeutic agents. In some embodiments, the one or more additional therapeutic agents is a beta blocker, an alpha-agonist, a carbonic anhydrase inhibitor, a prostaglandin or a prostaglandin-like compound, a miotic or cholinergic agent, an epinephrine compound, or a neuroprotective or anti-inflammatory compound. In some embodiments, the one or more additional therapeutic agents is a prostaglandin or a prostaglandin-like compound. In some embodiment, the prostaglandin-like compound is AR-102, latanoprost, bimatoprost, tafluprost, or travoprost.

Also provided herein are methods of treating an autoimmune disease in a subject in need thereof, comprising administering to the subject a compound, a composition, or a pharmaceutical composition provided herein.

In some embodiments, provided herein are methods of treating an autoimmune disease in a subject in need thereof, comprising administering to the subject a compound of one of the Formulae provided herein, or a pharmaceutically acceptable salt thereof.

In some embodiments, provided herein are methods of treating an autoimmune disease in a subject in need thereof, comprising administering to the subject a compound provided in Table 1, or a pharmaceutically acceptable salt thereof.

In some embodiments, the autoimmune disease is multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, or chronic obstructive pulmonary disease.

Compositions and Administration

The additional therapeutic agent or agents can be administered simultaneously or sequentially with the compounds of the present disclosure. Sequential administration includes administration before or after the compounds of the present disclosure. In some embodiments, the additional therapeutic agent or agents can be administered in the same composition as the compounds of the present disclosure. In other embodiments, there can be an interval of time between administration of the additional therapeutic agent and the compounds of the present disclosure.

In some embodiments, the administration of an additional therapeutic agent with a compound of the present disclosure will enable lower doses of the other therapeutic agents to be administered for a longer period of time.

Also provided herein are compositions comprising a compound provided herein, or a pharmaceutically acceptable salt thereof. In one embodiment, the compositions provided herein are pharmaceutical compositions comprising a pharmaceutically acceptable carrier.

Pharmaceutical compositions for use in accordance with the present disclosure may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection (including injection of a drug-eluting device either into the body as a whole, or into specific tissues of the eye), inhalation (either through the mouth or the nose), implants, or oral, buccal, parenteral or rectal administration. Techniques and formulations may generally be found in "Remington's Pharmaceutical Sciences," (Meade Publishing Co., Easton, PA).

The route by which the compounds of the present disclosure (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral, or by ocular injection into one of the chambers of the eye, such as intravitreal injection, intracameral injection, or injection into the aqueous humour.) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *Theobroma*. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include Avicel® RC-591 (from FMC Corporation of Philadelphia, PA) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds of the present disclosure and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this disclosure. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include injection, sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the disclosure, the compounds of the present disclosure are topically administered. Topical compositions that can be applied locally to the eye may be in any form known in the art, non-limiting Examples of which include solids, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye. Component B may further comprise one or more optional components.

An effective amount of a compound according to the present disclosure will vary with the particular condition being treated, the age and physical condition of the patient being treated, the severity of the condition, the duration of treatment, the nature of concurrent therapy, the route of administration, the particular pharmaceutically-acceptable carrier utilized, and like factors within the knowledge and expertise of the attending physician. For example, an effective amount of the compounds of the present disclosure for systemic administration is from about 0.01 to about 1000 μg/kg body weight, preferably from about 0.1 to about 100 μg/kg per body weight, most preferably form about 1 to about 50 μg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 ng/mL, more preferably from 0.05 to 50 ng/mL and most preferably from 0.1 to 10 ng/mL. While these dosages are based upon a daily administration rate, the compounds of the present disclosure may also be administered at other intervals, such as twice per day, twice weekly, once weekly, or once a month. One of ordinary skill in the art would be able to calculate suitable effective amounts for other intervals of administration.

The compounds of the present disclosure are useful in a method of reducing or decreasing intraocular pressure. The compounds of the present disclosure may be administered to a subject in need of treatment in an amount effective to reduce intraocular pressure. Thus, these compounds are useful in the treatment of glaucoma. The preferred route of administration for treating glaucoma is topically.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.001 to about 0.3%. If the $IC_{50}$ of the medicament is 10 nM, the amount of component A) will be from about 0.01 to about 1%. If the $IC_{50}$ of the medicament is 100 nM, the amount of component A will be from about 0.1 to about 10%. If the amount of component A is outside the ranges specified above (i.e., lower), efficacy of the treatment may be reduced. One skilled in the art understands how to calculate and understand an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this disclosure are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *Arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 1.5%, particularly, about 0.001 to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this disclosure include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this disclosure include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this disclosure include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In a particularly preferred embodiment of the disclosure, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to the range of 4.5-7.5 pH units.

Component A may be included in kits comprising a compound as described herein, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The disclosure will be further explained by the following illustrative Examples that are to be considered to be non-limiting.

EXAMPLES

Example 1: ROCK and JAK Assays

ROCK Kinase Inhibition Assays.

All compounds were initially prepared as 10 mM stocks in anhydrous dimethylsulfoxide (DMSO). A 20 μL aliquot of the 10 mM solutions was transferred to individual wells in column 1 of a 96-well polypropylene microtiter plate (Corning #3363) and diluted with DMSO to give a final compound concentration of 4 mM. Test compounds were then serially diluted 1:5 in DMSO for an 11-point concentration response and further diluted in the assay buffer bringing all compound concentrations to a final range of 100 μM to 10 μM in 2.5% DMSO. The assay was performed in white 96-well, flat-bottom, half-area, non-binding assay plate (Corning #3642) in assay buffer consisting of 20 mM HEPES (pH 7.5), 10 mM $MgCl_2$*$6H_2O$, 100 μM sodium orthovanadate, 0.05% CHAPS and 0.1% bovine serum albumin. A 10 μL aliquot of compound from each well of the intermediate dilution plate and 20 μL of a 2× substrate/enzyme solution containing acceptor substrate (800 nM RSK2 peptide KRRRLSSLRA (SEQ ID NO: 1)), ROCK2 enzyme (10 nM), or ROCK1 enzyme, and 1,4-Dithiothreitol (DTT, 2 uM) were added to all wells. The reaction was initiated by the addition of 10 μL of 4× stock solution ATP (2 μM). Reactions were thoroughly mixed manually, covered and allowed to incubate at room temperature for 75 min. Protein kinase activity was quantitated using Promega's KINASE-GLO™ luminescent Kinase Assay Kit according to the manufacturer's directions. ATP concentrations remaining in Test wells following the termination of the enzymatic reaction were compared against control wells containing equivalent amounts of DMSO containing no inhibitor (CTRL). ATP concentrations in both Test wells and CTRL wells were normalized against background (BKG) ATP concentrations in wells containing concentrations of inhibitor that completely inhibited the protein kinase under investigation (i.e. a concentration that prevented any consumption of ATP over the course of the incubation). Percent of Control (POC) values were determined for each concentration of compound tested according to the equation:

$$POC=((\text{Test well value}-BKG)/(CTRL-BKG))*100$$

$IC_{50}$ values were calculated using the following 4-parameter logistic curve-fitting algorithm:

$$f(x)=(A+((B-A)/(1+((x/C)^D))))$$

$IC_{50}$ values were converted to $K_i$ values using the following Cheng-Prusoff Equation:

$$K_i=IC_{50}/(1+([ATP]/Km\ ATP]))$$

JAK Kinase Assays.

Compounds were prepared in the exact same manner as described in the ROCK Kinase Assay with the exception to the substrate and enzyme. The JAK 2× substrate/enzyme solution consisted of acceptor substrate (800 nM Abl peptide EAIYAAPFAKKK (SEQ ID NO:2)), JAK2 or JAK3 enzyme (10 nM) and DTT (2 uM). All other steps and solutions remain identical to the ROCK Kinase Assay above. Results are shown above in Table 1.

Example 2. PTM-HTM Assay

Porcine Trabecular Meshwork cells (PTM) were isolated from freshly obtained enucleated porcine eyes. Immortalized Human Trabecular Meshwork cells (TM-1) were obtained through a kind gift from Donna Peters in the Department of Ophthalmology and Visual Sciences at the University of Wisconsin. Cells were plated onto fibronectin coated glass-bottom 96-well plates and allowed to attach overnight. Media was removed and replaced with test compound in media with 1% fetal bovine serum and incubated for various times. After incubation, cells were formaldehyde fixed, triton solubilized, and stained. PTM cells were stained with Alexa Fluor® 488 phalloidin (F-actin) and Hoechst 33342 (nuclei). TM-1 cells were stained with anti-paxillin followed by Alexa Fluor® 488 goat-anti-mouse IgG (focal adhesions) and Hoechst 33342 (nuclei). All staining reagents were obtained through Invitrogen. Images were collected on an INCell 2200 imager with a 20× objective. The actin fiber length and total area of focal adhesions were analyzed using custom algorithms developed in the INCell Developer Toolbox, v1.9.3. Data collected were converted to percent of control (untreated cells). Curves were fit to data in GraphPad Prizm using sigmoidal dose-response and constraining top and bottom to 100% and 0%, respectively.

Example 3

Topical pharmaceutical compositions for lowering intraocular pressure are prepared by conventional methods and formulated as shown in Table 7.

TABLE 7

| Ingredient | Amount (wt %) |
|---|---|
| heterobicyclic cyclopropanecarboxamide | 0.50 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 4.5-6.5 |
| Purified water | q.s. to 100% |

A compound provided herein is used as the heterobicyclic cyclopropanecarboxamide. When the composition is topically administered to the eyes once daily, the above composition decreases intraocular pressure in a subject suffering from glaucoma.

Example 4

Reference Example One. Pharmacological Activity for Glaucoma Assay

Pharmacological activity for glaucoma can also be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-phenyl-18, 19, 20-trinorprostaglandin $F_{2\alpha}$ Isopropyl Ester: Potential Anti-glaucoma Agents", *Journal of Medicinal Chemistry* 1995, 38 (2): 289-304.

While the disclosure has been described in detail and with reference to specific embodiments thereof, it will be apparent to one skilled in the art that various changes and modifications can be made without departing from the spirit and scope of the disclosure.

Groupings of alternative elements or embodiments disclosed herein may be referred to and claimed individually or in any combination with other members of the group or other elements found herein.

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended to be encompassed by the following claims.

What is claimed is:

1. A compound of the formula:

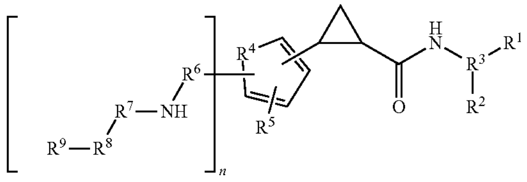

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: RSK2 peptide

<400> SEQUENCE: 1

Lys Arg Arg Arg Leu Ser Ser Leu Arg Ala
1 5 10

<210> SEQ ID NO 2
<211> LENGTH: 12
<212> TYPE: PRT
<213> ORGANISM: Artificial Sequence
<220> FEATURE:
<223> OTHER INFORMATION: Abl peptide

<400> SEQUENCE: 2

Glu Ala Ile Tyr Ala Ala Pro Phe Ala Lys Lys Lys
1 5 10

$R^2$ is H, halogen, $C_{1-6}$ alkyl, or $C_{1-6}$ haloalkyl;

$R^3$ is

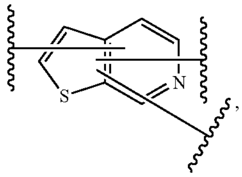

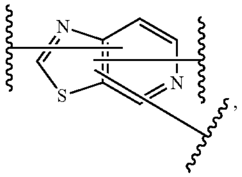

or

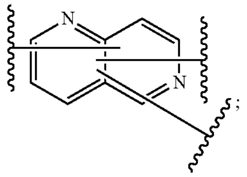

$R^4$ is S, —C(H)=C(H)—, or —C(H)=N—;

$R^5$ is H or halogen;

$R^6$ is CO or $SO_2$;

$R^7$ is a bond or $CH_2$;

$R^8$ is $CH_2$, phenyl, or a monocyclic $C_{3-5}$ heteroaryl having 1-3 heteroatoms, wherein each heteroatom is, independently, N, O, or S;

$R^9$ is H, halogen, CN, $NH_2$, OH, $C_{1-6}$ alkyl, $C_{1-6}$ alkyl-CN, $C_{1-6}$ haloalkyl, O—($C_{1-6}$ alkyl), O—($C_{1-6}$ haloalkyl), or $C_{3-6}$ cycloalkyl; and n is 0 or 1; or

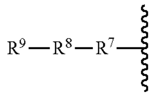

is H, and $R^{1-6}$ and n are as defined above.

2. A compound as in claim 1, wherein:

$R^1$ is H, F, Cl, Br, CN, $NH_2$, OH, $OCF_3$, $C_{1-6}$ alkyl, $C_{3-6}$ cycloalkyl, or $C_{1-6}$ haloalkyl;

$R^2$ is H, F, or $C_{1-3}$ alkyl; or $R^9$ is H, F, or $C_{1-3}$ alkyl.

3. A compound as in claim 1, wherein the compound is of the formula:

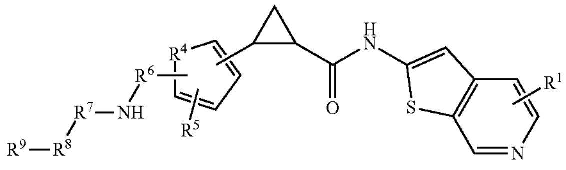

or a pharmaceutically acceptable salt thereof.

4. A compound as in claim 1, wherein the compound is of the formula:

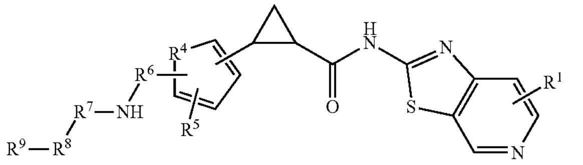

or a pharmaceutically acceptable salt thereof.

5. A compound as in claim 1, wherein the compound is of the formula:

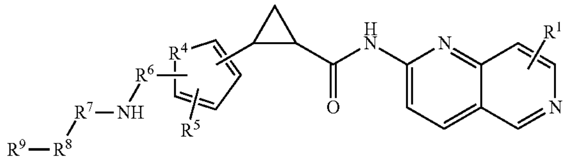

or a pharmaceutically acceptable salt thereof.

6. A compound as in claim 1, wherein $R^4$ is S.

7. A compound as in claim 1, wherein $R^4$ is —C(H)=C(H)—.

8. A compound as in claim 1, wherein $R^4$ is —C(H)=N—.

9. A compound as in claim 1, wherein $R^6$ is CO.

10. A compound as in claim 1, wherein $R^6$ is $SO_2$.

11. A compound as in claim 1, wherein $R^7$ is a bond.

12. A compound as in claim 1, wherein $R^7$ is a $CH_2$.

13. A compound as in claim 1, wherein $R^1$ is H, Cl or Me, $R^5$ is H, or $R^9$ is H.

14. A compound as in claim 1, wherein $R^8$ is phenyl.

15. A compound as in claim 1, wherein $R^8$ is a monocyclic $C_{3-5}$ heteroaryl having 1-3 heteroatoms, wherein each heteroatom is, independently, N, O, or S.

16. A compound as in claim 1, wherein $R^8$ is a monocyclic $C_{3-5}$ heteroaryl having 1-3 nitrogen atoms.

17. A compound as in claim 1, wherein:

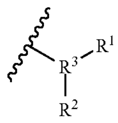

is

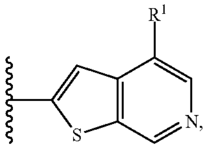

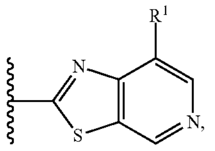

or

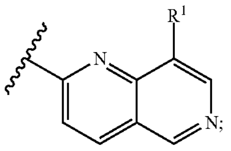

$R^1$ is H, F, Cl, $CH_3$, $CH_2OH$, $CH_2CH_3$, or CN;

$R^4$ is S, —C(H)=C(H)—, or —C(H)=N—;

$R^5$ is H;

$R^6$ is CO or $SO_2$;

$R^7$ is a bond or $CH_2$;

$R^8$ is phenyl, or a monocyclic $C_{4-5}$ heteroaryl having 1 or 2 nitrogen atoms;

$R^9$ is H or F; and n is 1.

18. A compound as in claim 1, wherein:
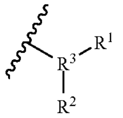
is
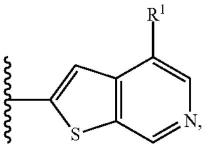
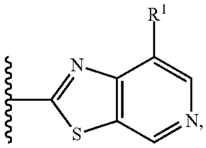
or
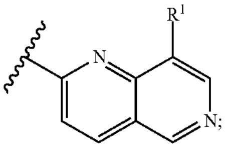
$R^1$ is H, F, CN, Cl, or $CH_3$;
$R^4$ is —C(H)═C(H)— or —C(H)═N—;
$R^5$ is H; and
n is 0.
19. A compound as in claim 1, wherein the compound is:
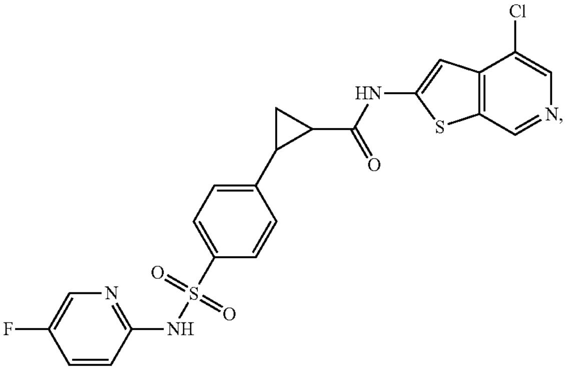
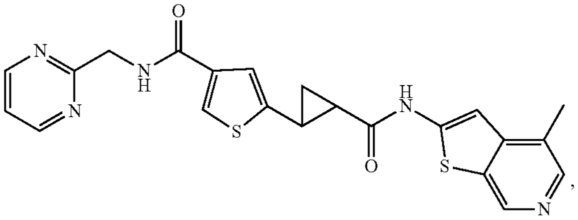
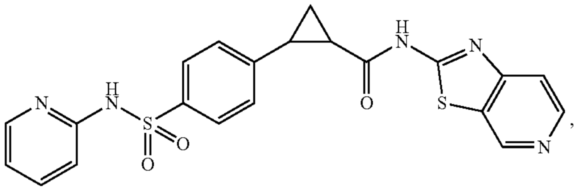
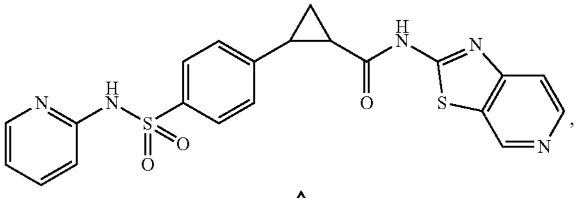
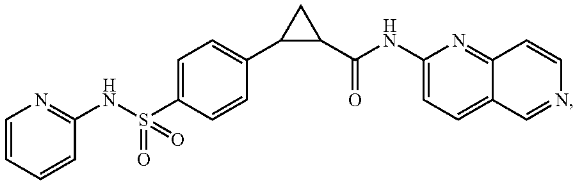
-continued
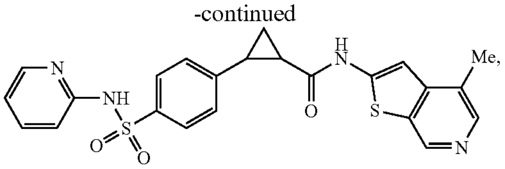
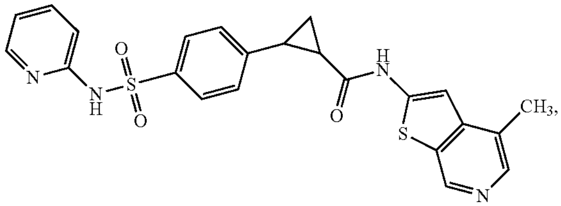
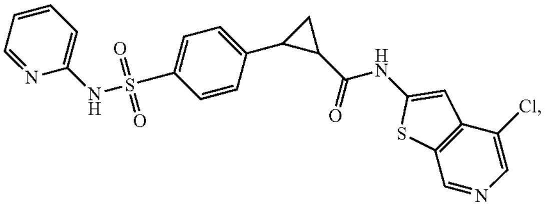
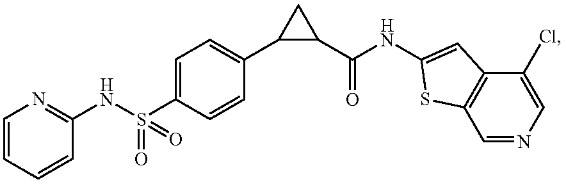
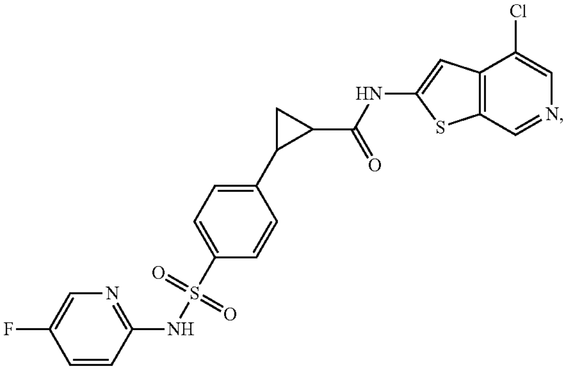
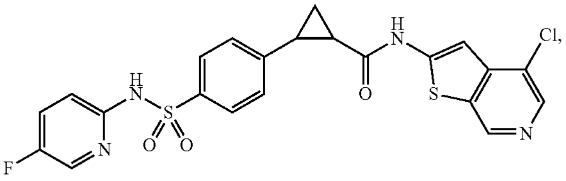
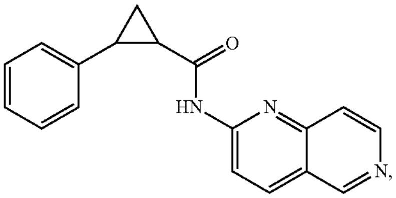
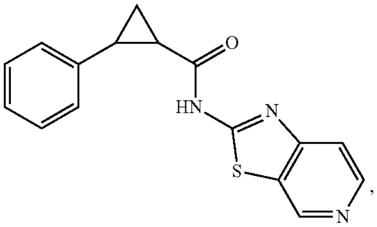

-continued
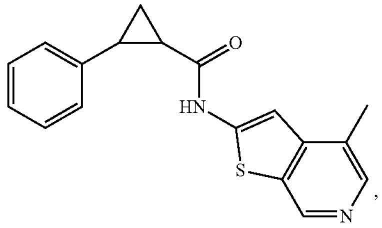
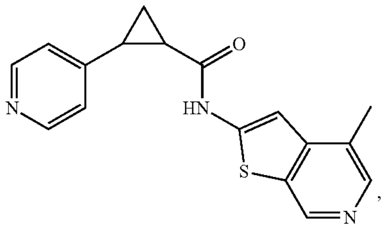
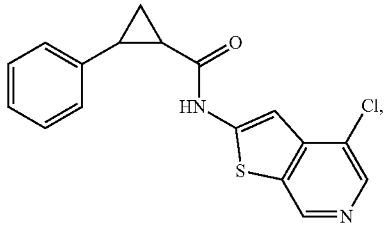
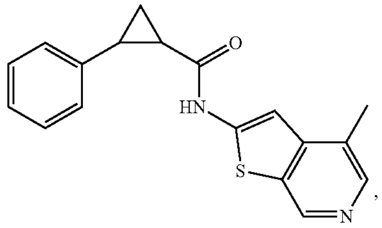
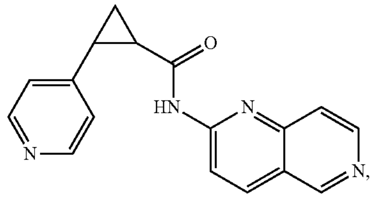
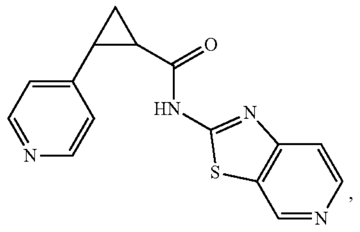
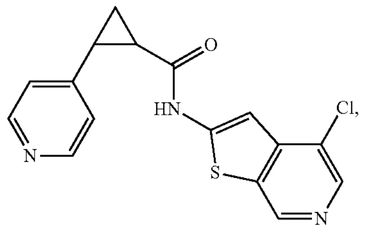
-continued
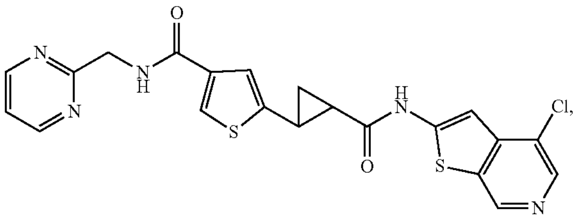
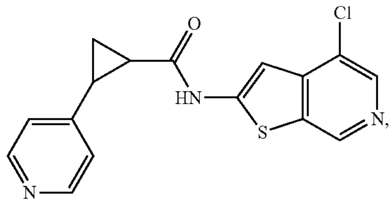
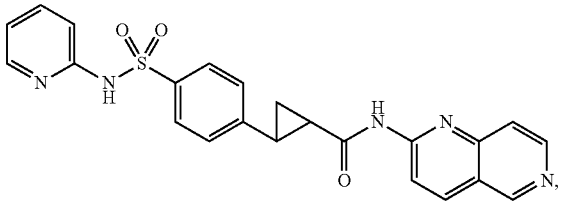
or a pharmaceutically acceptable salt thereof.
20. A compound as in claim 1, wherein the compound is of the formula:
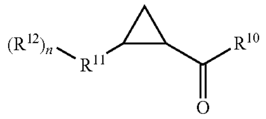
or a pharmaceutically acceptable salt thereof, wherein
n is 1;
$R^{10}$ is
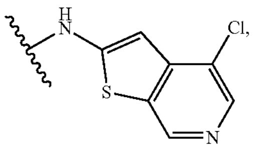
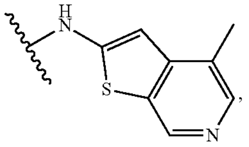
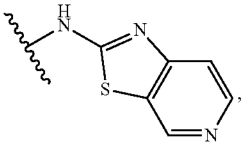
or
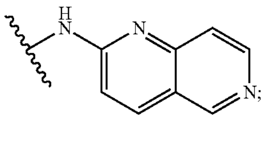

$R^{11}$ and $R^{12}$ are connected by an amide or sulfonamide linkage;

$R^{12}$ is

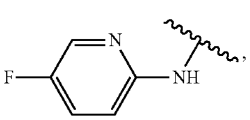,
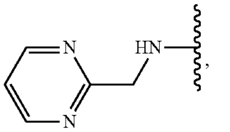,
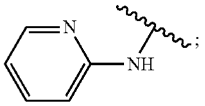;

and $R^{11}$ is

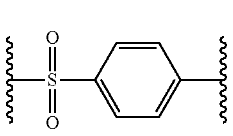 or 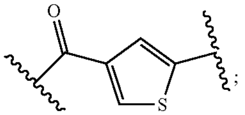;

or n is 0, $R^{10}$ and $R^{12}$ are as defined above, and $R^{11}$ is

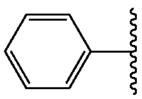 or 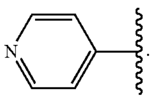.

21. A compound as in claim 1, wherein the compound is selected from:

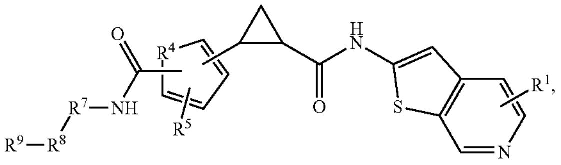

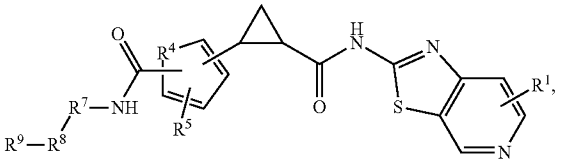

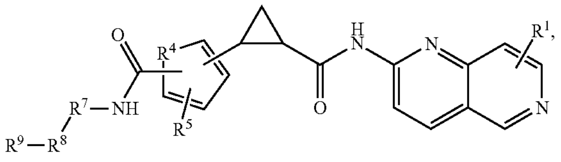

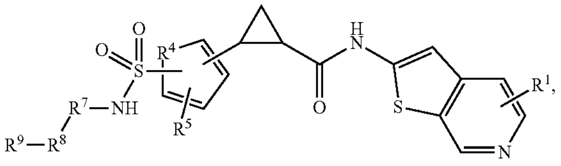

-continued

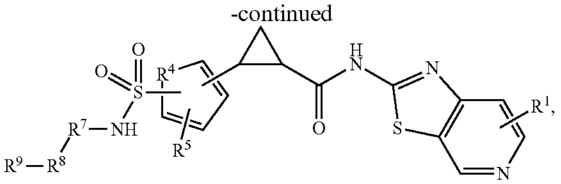

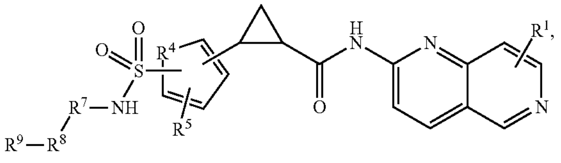

or a pharmaceutically acceptable salt thereof.

22. A compound as in claim 1, wherein:

$R^1$ is H, F, Cl, Br, I, CN, $NH_2$, OH, $OCF_3$, $OCH_2CF_3$, $C_{1-6}$ alkyl, $C_{3-6}$ cycloalkyl, or $C_{1-6}$ haloalkyl;

$R^2$ is H, F, Cl, Br, I, $C_{1-6}$ alkyl, or $C_{1-6}$ haloalkyl;

$R^3$ is

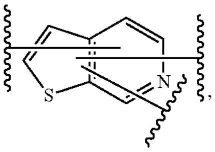, 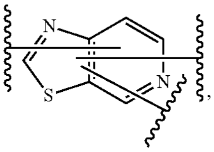, or

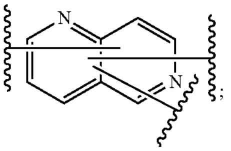;

$R^4$ is S, —C(H)═C(H)—, or —C(H)═N—;

$R^5$ is H, F, Cl, Br, or I;

$R^6$ is CO or $SO_2$;

$R^7$ is a bond or $CH_2$;

$R^8$ is phenyl, or a monocyclic $C_{3-5}$ heteroaryl having 1-3 heteroatoms, wherein each heteroatom is, independently, N, O, or S;

$R^9$ is H, F, Cl, Br, I, $C_{1-6}$ alkyl, or $C_{1-6}$ haloalkyl; and n is 0 or 1.

23. A compound of the formula:

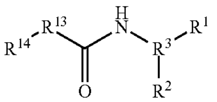

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

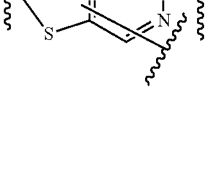, 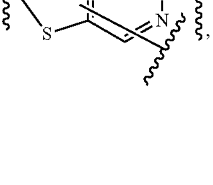, or

-continued

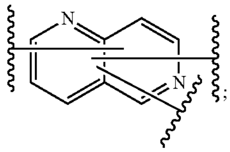;

$R^{13}$ is $CH_2$, $CH_2NH$,

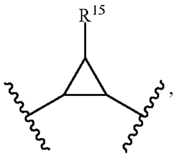, 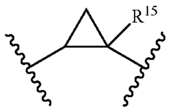,

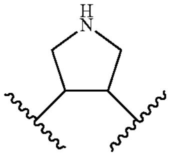, 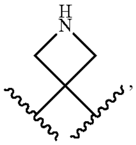, 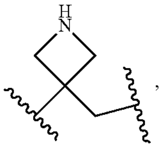,

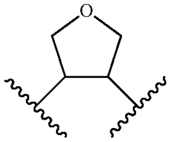, 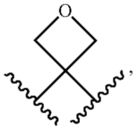, 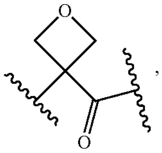,

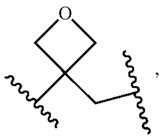, or 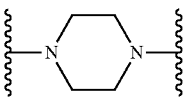;

$R^{14}$ is OH, $NH_2$, CN, $C_{1-3}$ alkyl, phenyl, phenyl-$CH_3$, $CH_2$-phenyl, phenyl-(O—$C_{1-6}$ alkyl), $SO_2$—($C_{1-6}$ alkyl), $CHCH_2$, $C_{1-3}$ alkylene-CN, $C_{1-6}$ alkyl-OH, $C_{1-6}$ alkyl-$NH_2$, a monocyclic $C_{3-5}$ heterocycloalkyl having 1-3 heteroatoms, or a monocyclic $C_{3-5}$ heteroaryl having 1-3 heteroatoms, wherein each heteroatom is, independently, N, O, or S, and wherein each heteroaryl may be substituted with one or two halogen substituents; and $R^{15}$ is H, CN, OH, or $NH_2$.

24. A compound of the formula:

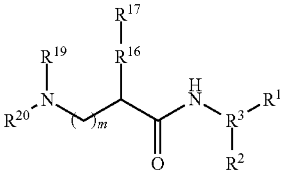

or a pharmaceutically acceptable salt thereof, wherein $R^1$ is H, halogen, CN, $NH_2$, OH, $C_{1-6}$ alkyl, $C_{1-6}$ haloalkyl, O—($C_{1-6}$ alkyl), O—($C_{1-6}$ haloalkyl), or $C_{3-6}$ cycloalkyl;

$R^2$ is H, halogen, $C_{1-6}$ alkyl, or $C_{1-6}$ haloalkyl;

$R^3$ is

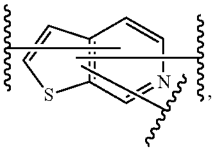, 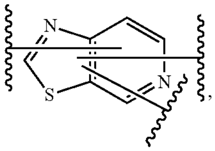, or

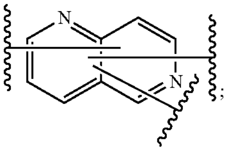;

$R^{16}$ is phenyl, $CH_2$-phenyl, a $CH_2$-monocyclic $C_{3-5}$ heteroaryl having 1-3 heteroatoms, or a monocyclic $C_{3-5}$ heteroaryl having 1-3 heteroatoms, wherein each heteroatom is, independently, N, O, or S, and wherein each heteroaryl may be substituted with one or two halogen substituents;

$R^{17}$ is H, OH, halogen, $C_{1-6}$ alkyl-OH, $C_{1-6}$ alkyl-O—C(O)-phenyl-$(R^{18})_z$;

$R^{18}$ is H, OH, halogen, or $C_{1-6}$ alkyl;

$R^{19}$ is H or $C_{1-6}$ alkyl;

$R^{20}$ is H or $C_{1-6}$ alkyl;

z is 0, 1, 2, 3, 4, or 5; and m is 0, 1, or 2.

25. A compound, selected from

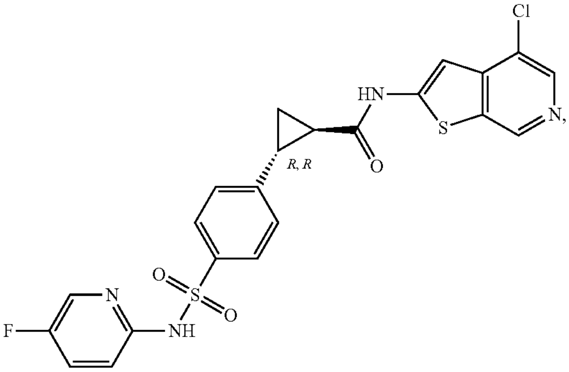,

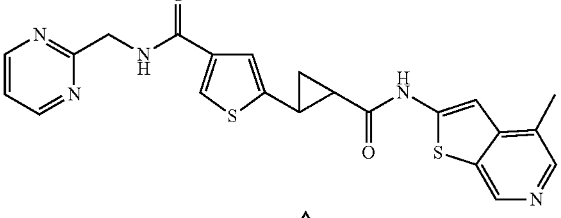,

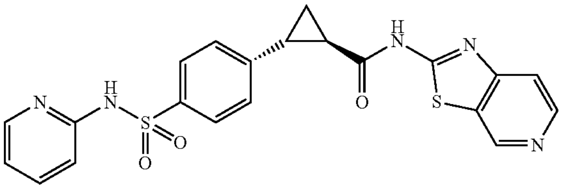,

-continued
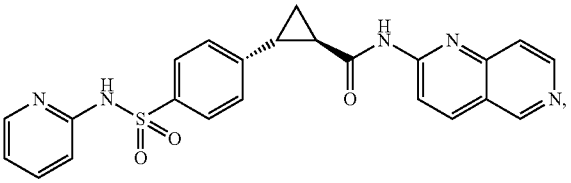
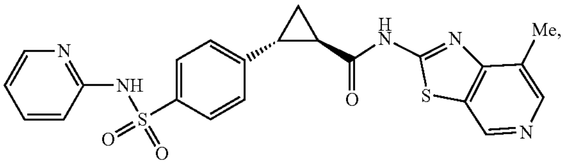
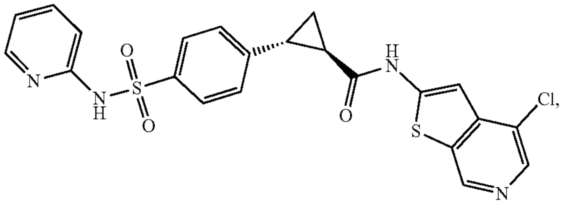
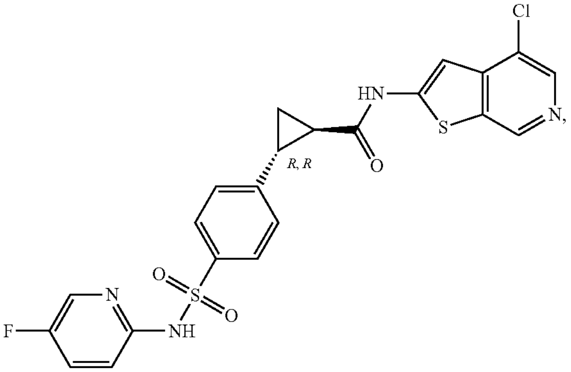
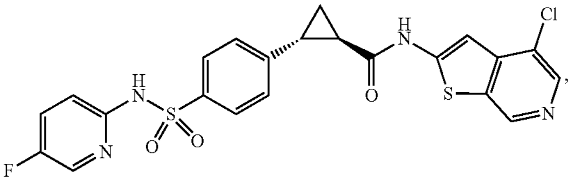
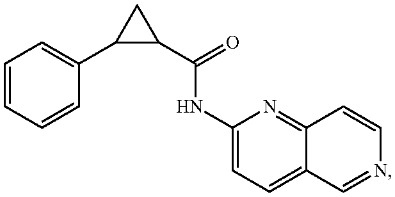
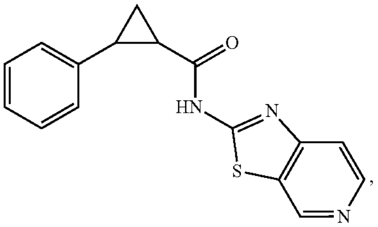
-continued
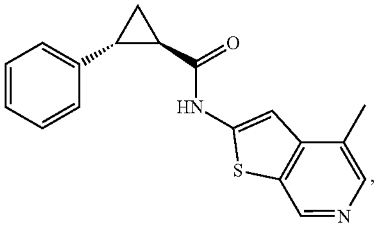
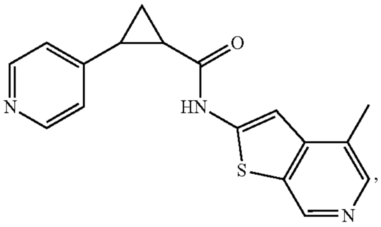
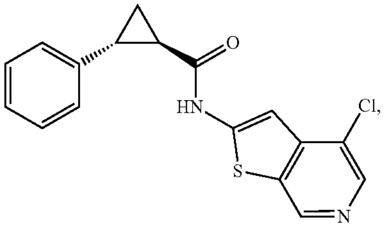
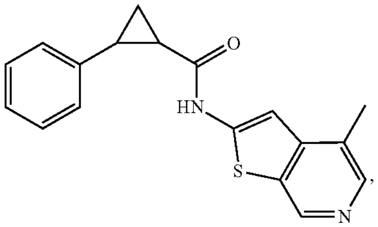
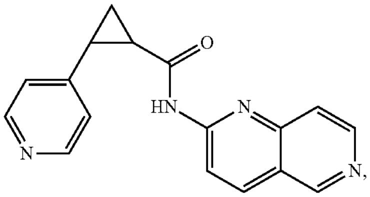
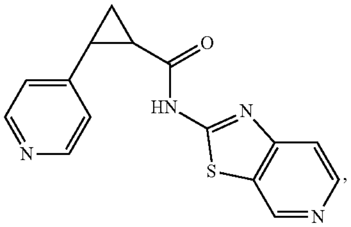
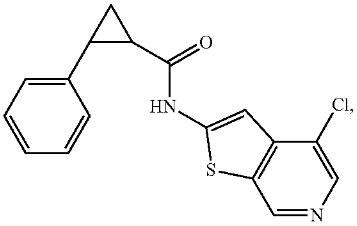

-continued
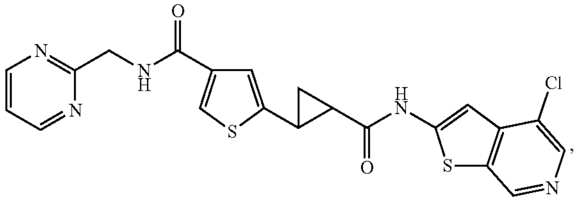
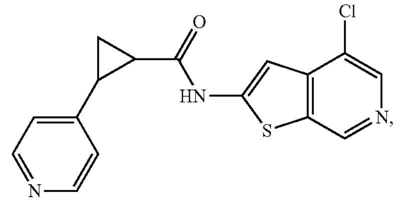
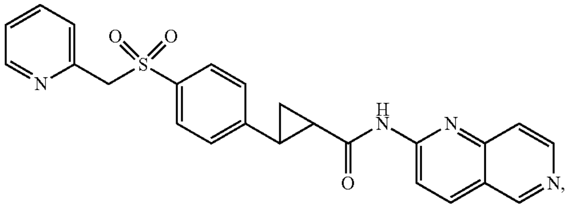
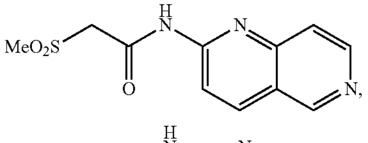
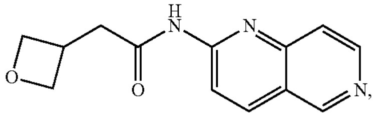
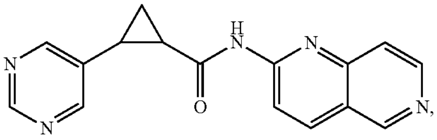
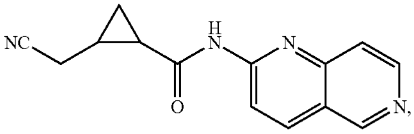
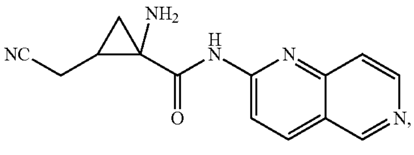
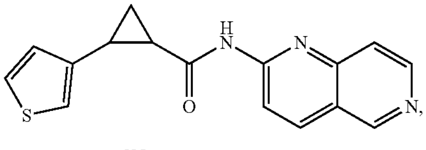
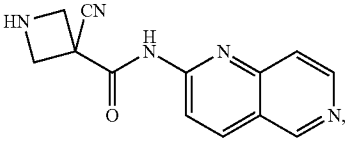
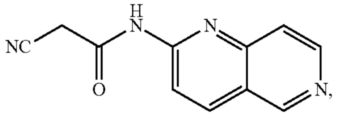
-continued
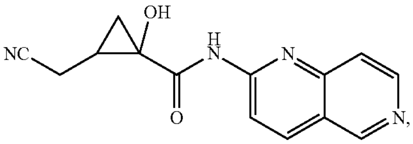
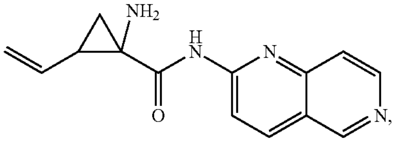
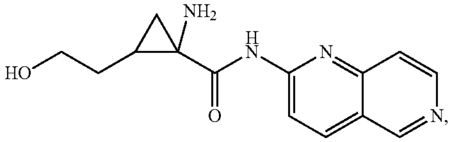
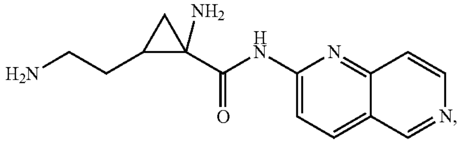
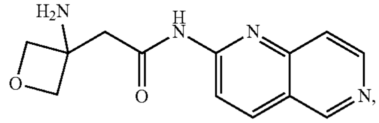
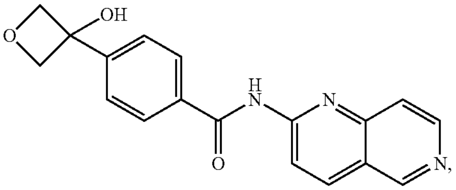
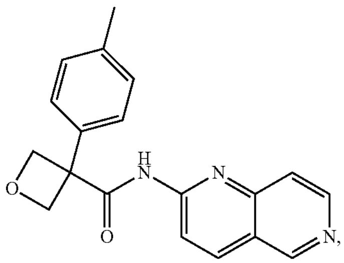
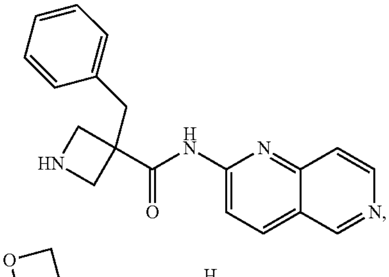
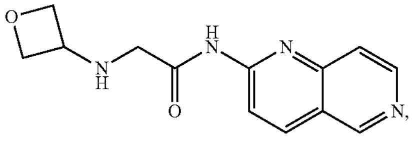
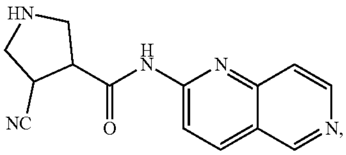

-continued
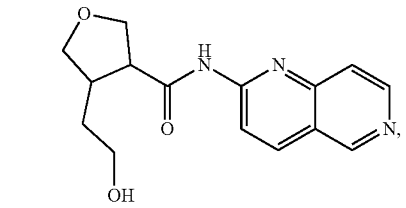
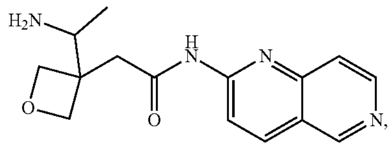
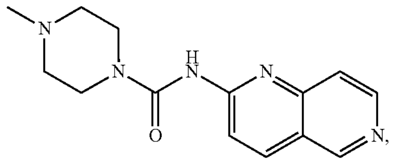
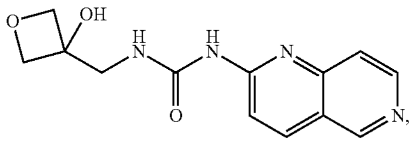
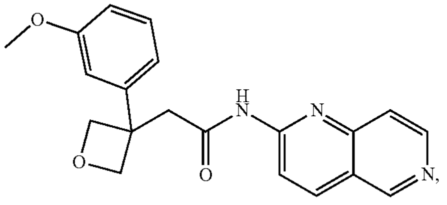
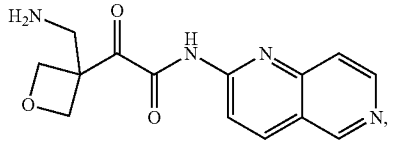
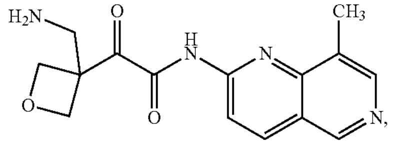
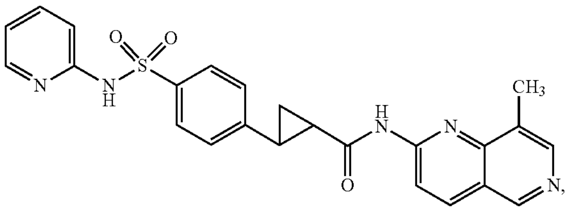
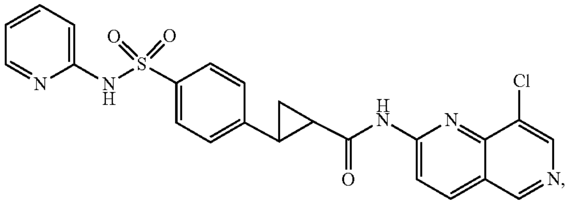
-continued
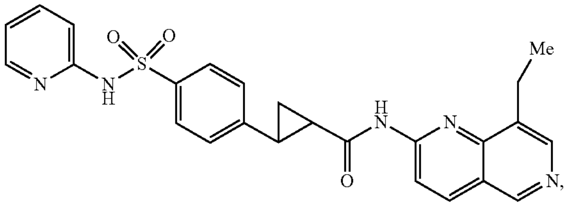
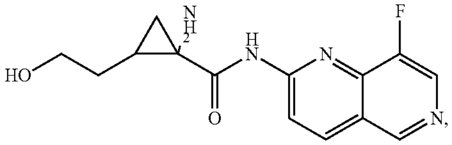
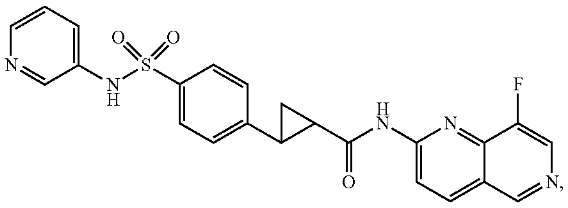
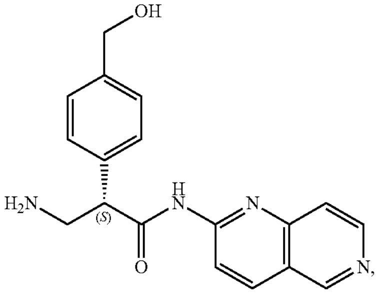
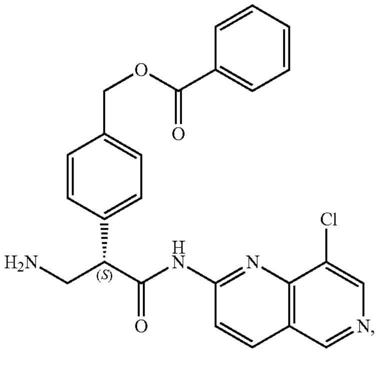
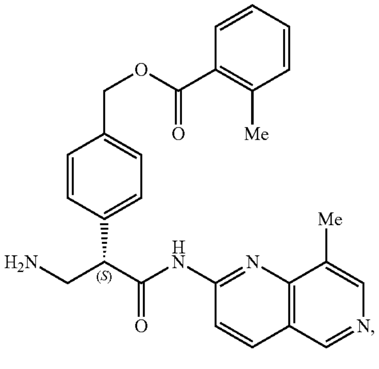

-continued
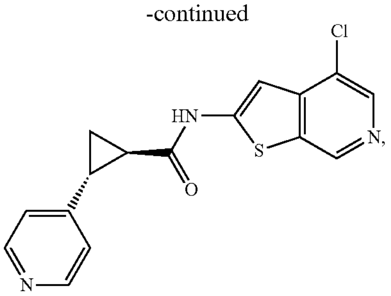
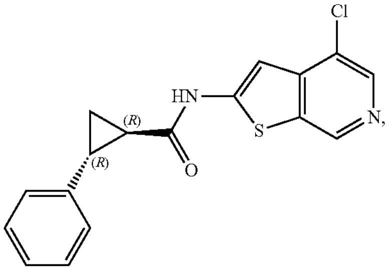
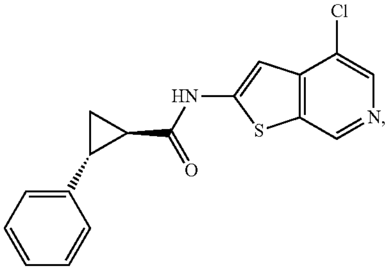
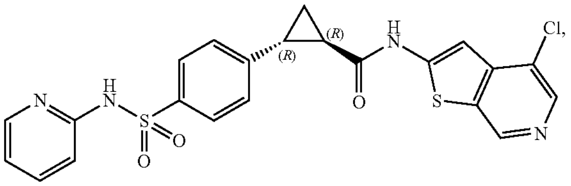
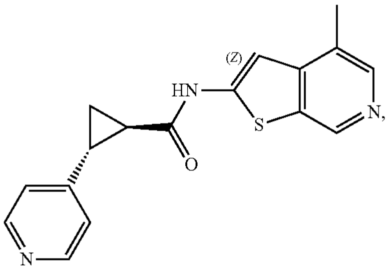
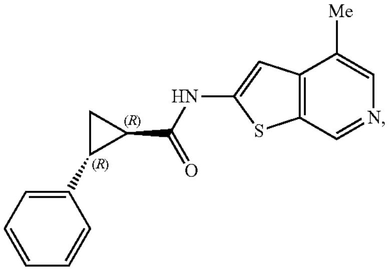
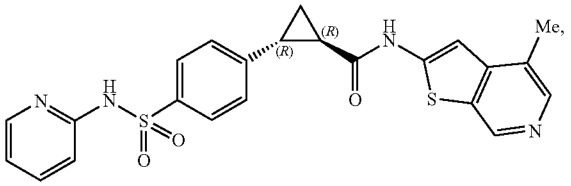
-continued
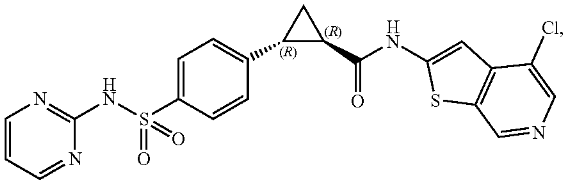
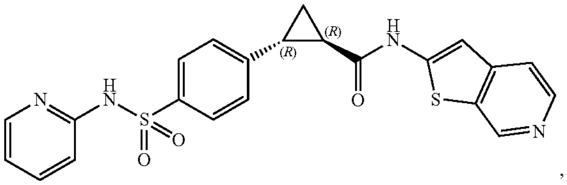
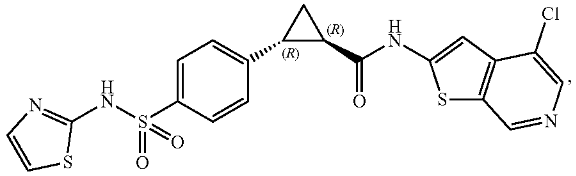
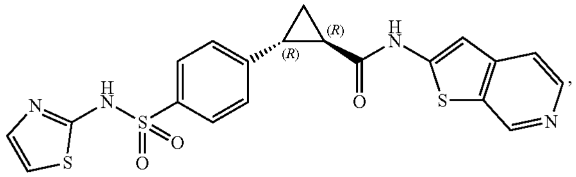
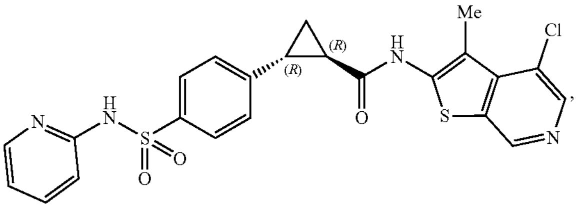
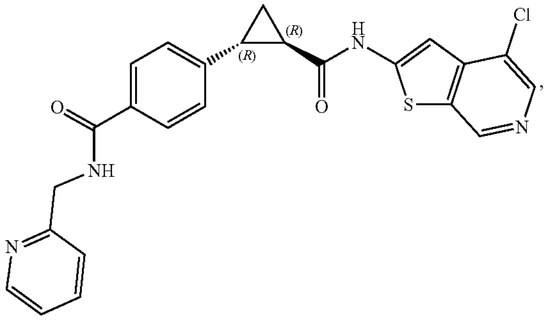
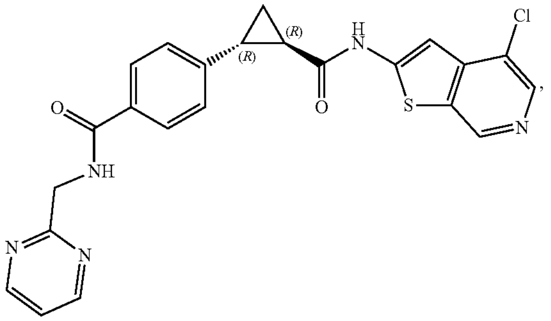

-continued
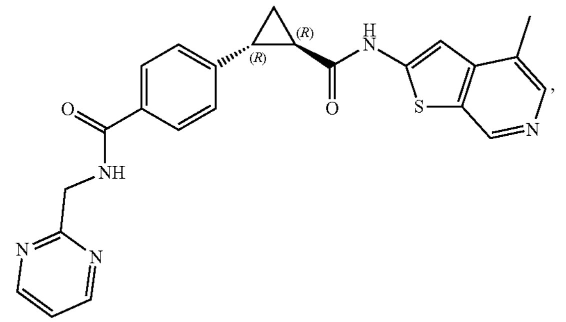
,
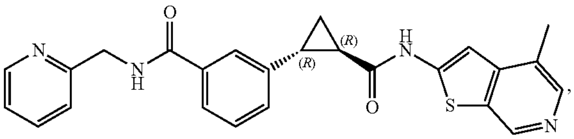
,
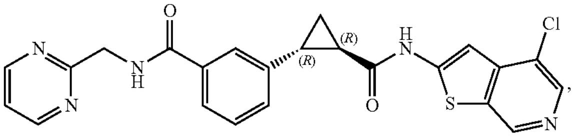
,
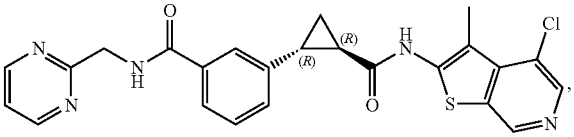
,
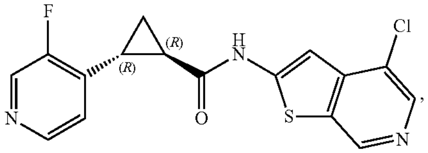
,
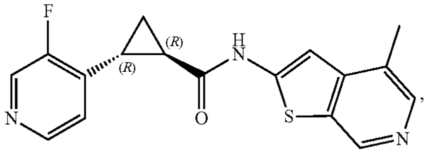
,
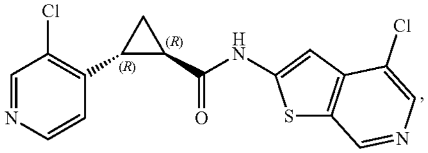
,
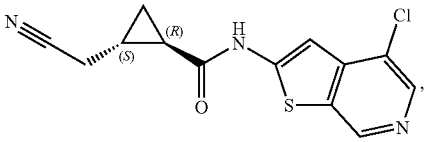
,
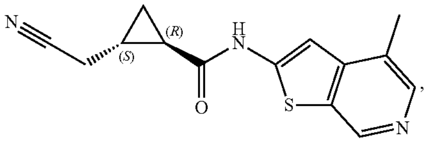
,
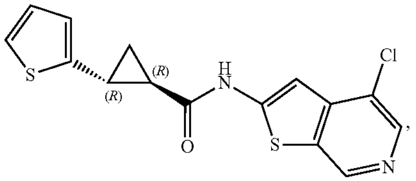
,
-continued
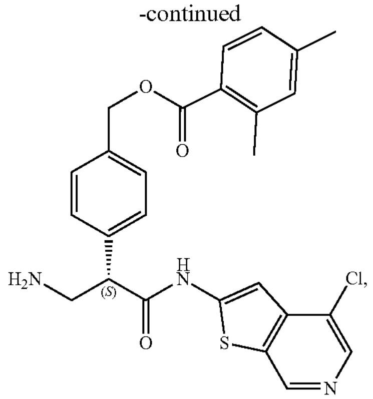
,
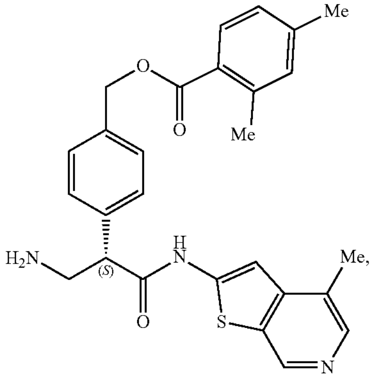
,
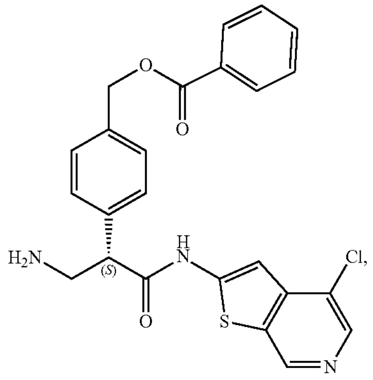
,
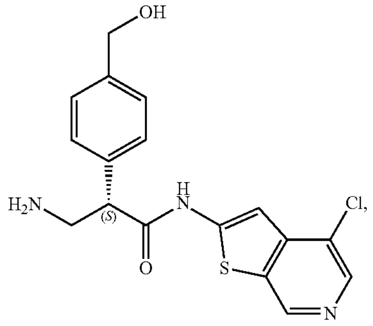
, -continued
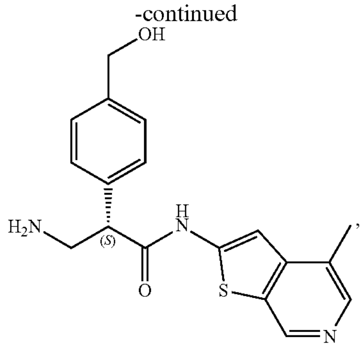
,
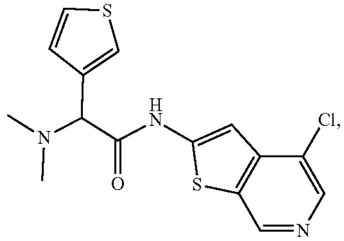
,
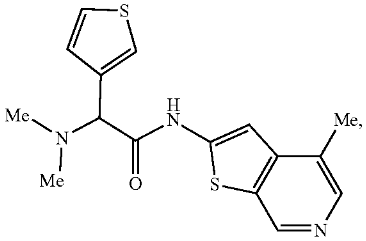
,
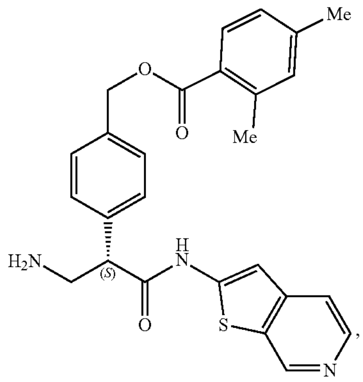
,
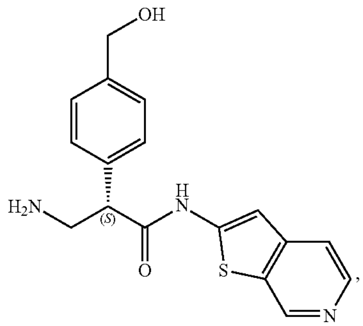
,
-continued
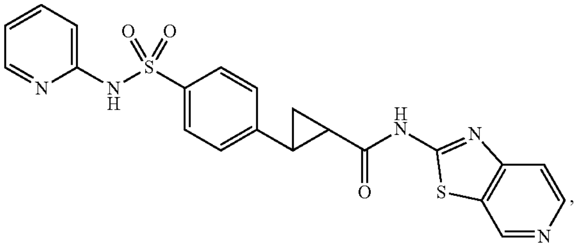
,
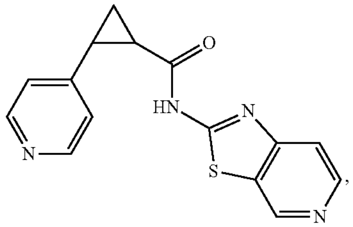
,
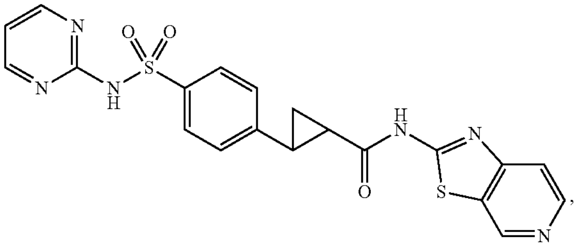
,
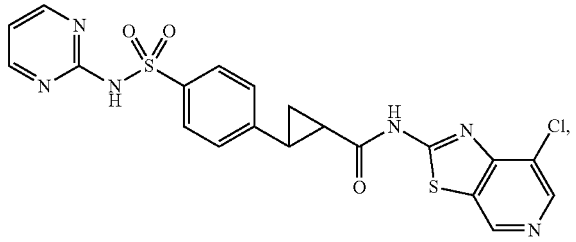
,
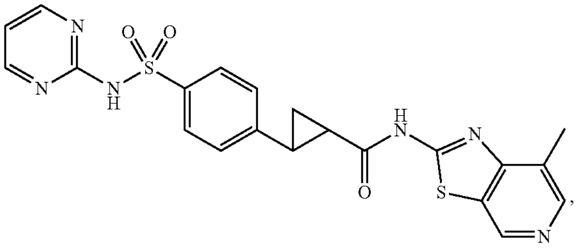
,
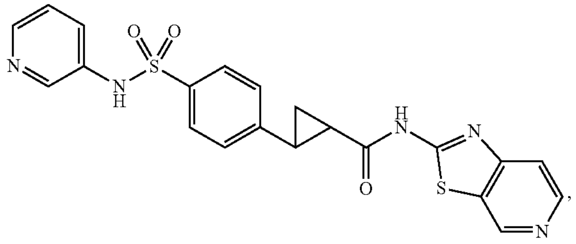
,
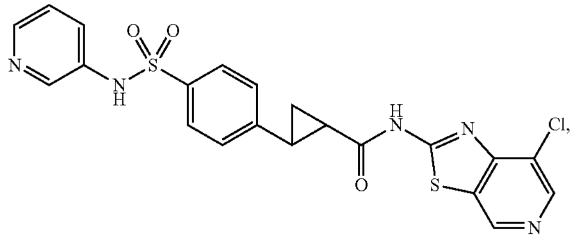

-continued
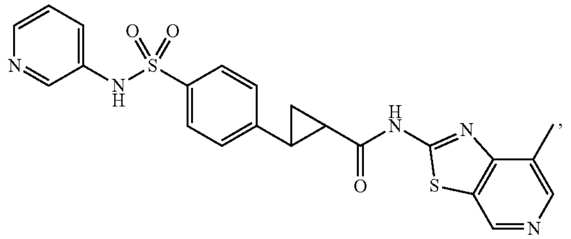
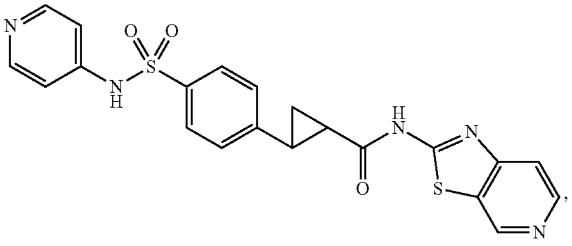
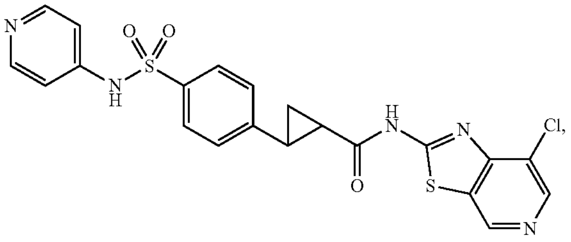
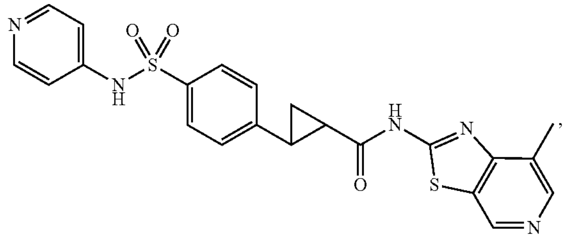
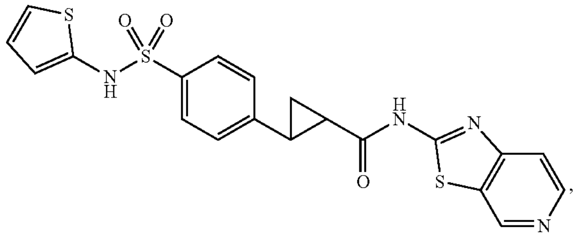
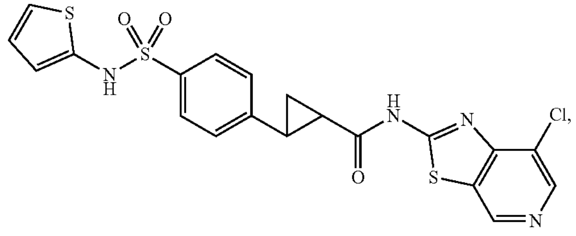
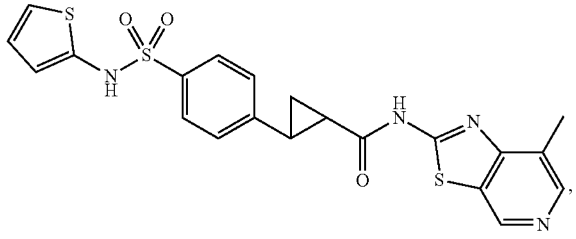
-continued
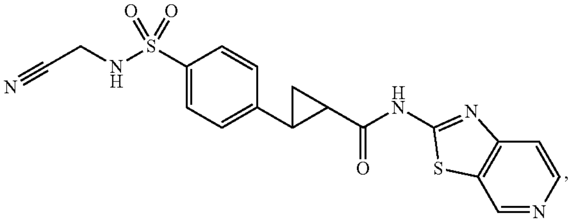
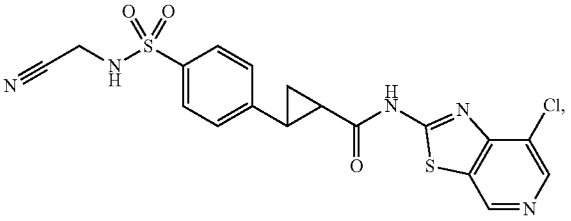
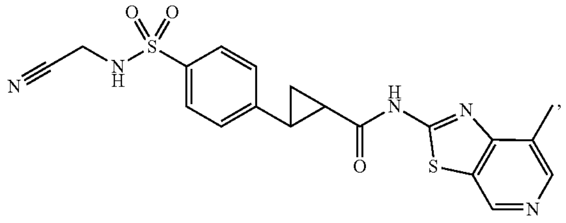
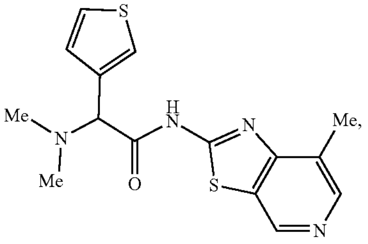
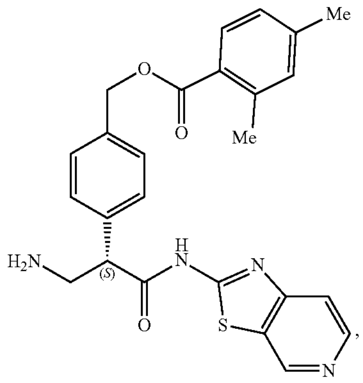
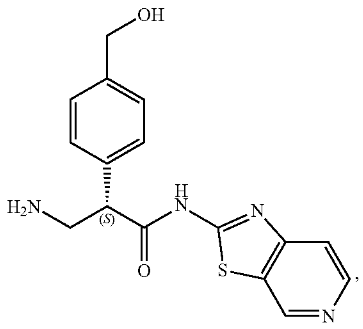

-continued

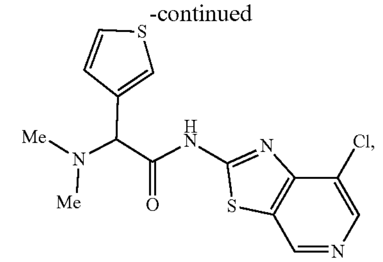

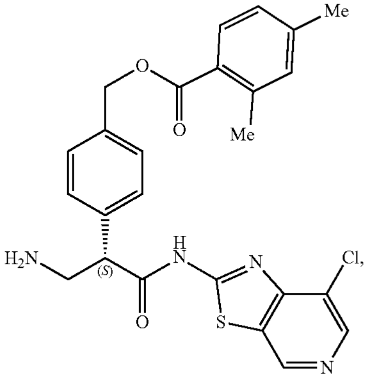

or

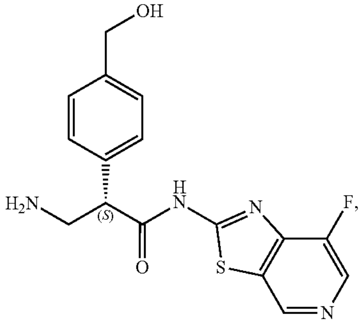

or a pharmaceutically acceptable salt thereof.

26. A method of treating glaucoma in a subject in need thereof, comprising administering to the subject a compound as in claim 1.

27. A method of treating glaucoma in a subject in need thereof, comprising administering to the subject a compound as in claim 19.

28. A method of treating glaucoma in a subject in need thereof, comprising administering to the subject a compound as in claim 23.

29. A method of treating glaucoma in a subject in need thereof, comprising administering to the subject a compound as in claim 24.

30. A method of treating glaucoma in a subject in need thereof, comprising administering to the subject a compound as in claim 25.

31. A method as in claim 26, wherein the administering is topically to an eye of the subject.

32. A method as in claim 27, wherein the administering is topically to an eye of the subject.

33. A method as in claim 28, wherein the administering is topically to an eye of the subject.

34. A method as in claim 29, wherein the administering is topically to an eye of the subject.

35. A method as in claim 30, wherein the administering is topically to an eye of the subject.

36. A method of reducing intraocular pressure in a subject in need thereof, comprising administering to the subject a compound as in claim 1.

37. A method of reducing intraocular pressure in a subject in need thereof, comprising administering to the subject a compound as in claim 19.

38. A method of reducing intraocular pressure in a subject in need thereof, comprising administering to the subject a compound as in claim 23.

39. A method of reducing intraocular pressure in a subject in need thereof, comprising administering to the subject a compound as in claim 24.

40. A method of reducing intraocular pressure in a subject in need thereof, comprising administering to the subject a compound as in claim 25.

41. A method as in claim 36, wherein the administering is topically to an eye of the subject.

42. A method as in claim 37, wherein the administering is topically to an eye of the subject.

43. A method as in claim 38, wherein the administering is topically to an eye of the subject.

44. A method as in claim 39, wherein the administering is topically to an eye of the subject.

45. A method as in claim 40, wherein the administering is topically to an eye of the subject.

* * * * *